United States Patent [19]
Pang et al.

[11] Patent Number: 6,110,702
[45] Date of Patent: Aug. 29, 2000

[54] PSA POSITIVE REGULATING (PSAR) SEQUENCES AND USES THEREOF

[75] Inventors: Shen Pang, Van Nuys; Arie S. Belldegrun, Los Angeles, both of Calif.

[73] Assignee: The Regents of the University of California, Oakland, Calif.

[21] Appl. No.: 08/828,972

[22] Filed: Mar. 27, 1997

Related U.S. Application Data

[60] Provisional application No. 60/014,201, Mar. 27, 1996.

[51] Int. Cl.[7] .............................. C12P 21/06; C12P 21/04; C12N 15/00; C07H 21/04
[52] U.S. Cl. .................... 435/69.1; 435/70.1; 435/320.1; 435/455; 435/466; 536/24.1
[58] Field of Search .............................. 536/24.1; 514/44; 435/69.1, 70.1, 455, 466, 320.1

[56] References Cited

U.S. PATENT DOCUMENTS

| | | | |
|---|---|---|---|
| 5,648,478 | 7/1997 | Henderson | 536/241 |
| 5,698,443 | 12/1997 | Henderson et al. | 435/320.1 |

FOREIGN PATENT DOCUMENTS

| | | |
|---|---|---|
| WO 95/19434 | 7/1995 | WIPO . |
| WO 97/01358 | 1/1997 | WIPO . |

OTHER PUBLICATIONS

Pang, S. et al., "Identification of a Positive Regulatory Element Responsible for Tissue–specific Expression of Prostate–specific Antigen," *Cancer Research*, 57:459–499, Feb. 1, 1997. (Exhibit 2).

Dannull, J. et al., "Development of Gene Therapy for Prostate Cancer Using a Novel Promoter of Prostate–specific Antigen," *British Journal of Urology*, 79:97–103, 1997 (Exhibit 3).

Cleutjens, Kitty B.J.M. et al., "An Androgen Response Element in a Far Upstream Enhancer Region Is Essential for High, Androgen–Regulated Activity of the Prostate–specific Antigen Promoter," *Molecular Endocrinology*, 11(2):148–161, 1997. (Exhibit 4).

Pang et al., 1995, Human Gene Therapy, 6:1417–1426.

Riegman et al., 1991, Molecular Endocrinology, 5(12):1921–1930.

Bacchetti and Graham, 1977, PNAS USA, 74:1590–1594.

Li and Steshenko, 1992, Journal of Immunology, 148(3):788–94.

Kay et al., 1991, J. Exp. Med., 173:775–778.

Shuur et al., 1996, J. Biol. Chem. 271:7043–7051.

Vile et al., 1994, Cancer Res. 54:6228–6234.

el–Shirbiny, A.M., 1994, Adv. Clin. Chem. 31:99–133.

*Primary Examiner*—Yvonne Eyler
*Attorney, Agent, or Firm*—Mandel & Adriano

[57] ABSTRACT

The present invention provides an isolated nucleic acid molecule which is a PSA positive regulatory sequence (PSAR). This molecule has been deposited with the ATCC. In one embodiment of the invention, the molecule comprises a nucleic acid sequence shown in FIG. 4 (SEQ ID NO: 3).

40 Claims, 10 Drawing Sheets

FIG. 4

```
   1 CTGCAGAGAA ATTAATTGTG GCCTGATGTC CCTGTCCTGG AGAGGGTGGA GGTGGACCTT
1067 CTGCAGAGAA ATTAATTGTG GCCTGATGTC CCTGTCCTGG AGAGGGTGGA GGTGGACCTT

61 CACTAACCTC CTACCTTGAC CCTCTCTTTT AGGGCTCTTT CTGACCTCCA CCATGATACT
1127 CACTAACCTC CTACCTTGAC CCTCTCTTTT AGGGCTCTTT CTGACCTCCA CCATGGTACT

121 AGGACCCCAT TGTATTCTGT ACACTCTTGA CTCTATGACC CCCACTGCCC ACTGCATCCA
1187 AGGACCCCAT TGTATTCTGT ACCCTCTTGA CTCTATGACC CCCACTGCCC ACTGCATCCA

181 GCTGGGTCCC CTCCTATCTC TATTCCCAGC TGGCCAGTGC AGTCTCAGAG CCCACCTGTT
1247 GCTGGGTCCC CTCCTATCTC TATTCCCAGC TGGCCAGTGC AGTCTCAGTG CCCACCTGTT

241 TGTCAGTTAC TCTGAAGGGG CTGACATTTT ACTGACTTGC AAACAAATAA GCTAACTTTC
1307 TGTCAGTAAC TCTGAAGGGG CTGACATTTT ACTGACTTGC AAACAAATAA GCTAACTTTC

301 CAGAGTTTTG TGAATGTTGG CAGAGTCCAT GAGACTCCTG AGTCAGAGGC AAAGGCTTTT
1367 CAGAGTTTTG TGAATGCTGG CAGAGTCCAT GAGACTCCTG AGTCAGAGGC AAAGGCTTTT

361 ACTGCTCACA GCTTAGCAGA CAGCATGAGG TTCATGTTCA CATTAGTACA CCTTGCCCCC
1427 ACTGCTCACA GCTTAGCAGA CAGCATGAGG TTCATGTTCA CATTAGTACA CCTTGCCCCC

421 CCCAAATCTT GTAGGGTGAC CAGAGCAGTC TAGGTGGATG CTGTGCACAC GGGGTTTGTG
1487 CCCAAATCTT GTAGGGTGAC CAGAGCAGTC TAGGTGGATG CTGTGCAGAA GGGGTTTGTG

481 CCACTGGTGA GAAACCTGAG ATTAGGAATC CTCAATCTTA TACTGGGACA ACTTGCAAAC
1547 CCACTGGTGA GAAACCTGAG ATTAGGAATC CTCAATCTTA TACTGGGACA ACTTGCAAAC

541 CTGCTCAGCC TTTGTCTCTG ATGAAGATAT TATCTTCATG ATCTTGGATT GAAAACAGAC
1607 CTGCTCAGCC TTTGTCTCTG ATGAAGATAT TATCTTCATG ATCTTGGATT GAAAACAGAC

601 CTACTCTGGA GGAACATATT GTATTGATTG TCCTTGACAG TAAACAAATC TGTTGTAAGA
1667 CTACTCTGGA GGAACATATT GTATCGATTG TCCTTGACAG TAAACAAATC TGTTGTAAGA

661 GACATTATCT TTATTATCTA GGACAGTAAG CAAGCCTGGA TCTGAGAGAG ATATCATCTT
1727 GACATTATCT TTATTATCTA GGACAGTAAG CAAGCCTGGA TCTGAGAGAG ATATCATCTT

721 GCAAGGATGC CTGCTTTACA AACATCCTTG AAACAACAAT CCAGAAAAAA A--GGTGTTG
1787 GCAAGGATGC CTGCTTTACA AACATCCTTG AAACAACAAT CCAGAAAAAA AAAGGTGTTG

779 CTGTCTTTGC TCAGAAGACA CACAGATACG TGACAGAACC ATGG    822
1847 CTGTCTTTGC TCAGAAGACA CACAGATACG TGACAGAACC ATGG    1990
```

PSA POSITIVE REGULATING (PSAR) SEQUENCES AND USES THEREOF

This application is based on a provisional application, U.S. Serial No. 60/014,201, filed Mar. 27, 1996.

Throughout this application various publications are referenced. The disclosures of these publications in their entireties are hereby incorporated by reference into this application in order to more fully describe the state of the art to which this invention pertains.

BACKGROUND OF THE INVENTION

A protein specifically expressed in the prostate has been identified and characterized as the prostate-specific antigen (PSA) (Hara, M. and Kimura, H. (1989) Two prostate-specific antigens, γ-seminoprotein and β-microseminoprotein, Lab. Clin. Med. 113:541–548; Wang, M. C. et al. (1979) Purification of a human prostate specific antigen, Investigative Urology 17:159–163; Chan, D. W. et al. (1987) Prostate-specific antigen as a marker for prostatic cancer: a monoclonal and a polyclonal immunoassay compared, Clinical Chemistry 33:1916–1920; Emtage, L. A. et al. (1987) The role of prostate specific antigen in the baseline assessment of patients undergoing hormone therapy for advanced prostate cancer, British Journal of Urology 60:572–577.)

The tissue specific expression of this protein implies the existence of a unique mechanism by which the PSA gene can be transcribed only in prostate cells. The 5', ≈620 bp, flanking sequence of the PSA gene was studied and identified as the promoter for the PSA gene (Riegman, P. H. et al. (1991). The promoter of the prostate-specific antigen gene contains a functional androgen responsive element, Molecular Endocrinology 5:1921–1930). Using electroporation methods to transfect LNCaP prostate cell line, the PSA promoter isolated from a prostate carcinoma patient (PCPSA-P) has shown strong tissue specificity and responsiveness to androgen stimulation (Pang S, et al. (1995). Prostate tissue specificity of the prostate-specific antigen (PSA) promoter isolated from a patient with prostate cancer, Human Gene Therapy 6:1417–1426).

The very high expression of the PSA gene in some patients (more than 1000-fold increase in some cases) with advanced prostate cancer suggests that the regulation of PSA gene expression may involve other DNA sequences besides the PSA promoter. In other words, the transcription of PSA gene may be synergistically controlled by two regulatory elements. Similar cases have been reported for other genes.

A tissue-specific distal promoter for the human skeletal alpha-actin gene has been found in myogenic cells, and deletion of this distal promoter results in a ten-fold reduction in transcription (Muscat, G. E.; Perry, S., Prentice, H.; Kedes, L.; The human skeletal alpha-actin gene is regulated by a muscle-specific enhancer that binds three nuclear factors, Gene Expression 2:111–126). It is possible that PSA gene expression is controlled in a similar manner.

Addition of a distal PSA promoter or positive regulatory sequence should likely increase promoter activity without compromising its tissue specificity. Since gene expression is usually controlled by both promoter and enhancer, there may also be a prostate tissue-specific enhancer in the flanking regions of the PSA gene.

Using polymerase chain reaction (PCR) cloning methods, a DNA sequence upstream of the PSA promoter was amplified and obtained. The resulting DNA fragment was cloned into a plasmid containing the PSA promoter and luciferase gene. The resulting construct was tested using both lipofection and electroporation to introduce them into PSA-producing prostate cell line LNCaP and control cell lines including non-PSA-producing cell line PC-3 and DU145, renal cell line R11 and breast tumor cell line MCF-7.

Deletion tests were performed in order to define the essential region of the regulatory element. A potent tissue-specific DNA fragment of approximately 820 bp was identified, called the prostate specific antigen promoter (PSAP; Riegman, P. H. J. et al. (1991). The promoter of the prostate-specific antigen gene contains a functional androgen responsive element, Mol. Endocrinol. 5(12):1921–1930). PSAP has been identified, characterized and found to be a tissue specific promoter regulating PSA gene expression.

The discovery herein involves identifying additional regulatory sequences. Sequences upstream of the PSA promoter were screened and a DNA fragment of 822 base pairs (bp) positively regulating gene expression was found in PSA-producing prostate cells. This 822 bp DNA fragment is a newly identified PSA gene regulatory sequence (PSAR). PSAR in combination with our previously identified PSA promoter (PCPSA-P) exhibited maximal activity using DNA transfection by electroporation in PSA–producing LNCaP cell line.

With the addition of 10 to 100 nM dihydrotestosterone (DHT), a more than 1000-fold higher expression of transgene was observed compared to androgen negative control. In contrast to very high expression in the LNCaP cell line, the PSAR-PCPSA-P vector demonstrated minimal expression in non-PSA-producing prostate cell line PC-3, renal tumor cell line R11, breast cancer cell line MCF-7 and cervical adenocarcinoma cell line HeLa.

The high tissue specificity and androgen responsiveness of the combined construct, which consists of the newly identified DNA sequence and PCPSA-P, provide a solid foundation to generate gene therapy vectors for prostate cancer gene therapy.

SUMMARY OF THE INVENTION

The present invention provides an isolated nucleic acid molecule which is a PSA positive regulatory sequence (PSAR). In one embodiment of the invention, the molecule comprises a nucleic acid sequence shown in the top line of FIG. 4 (SEQ ID No: 3). In another embodiment, the molecule comprises a PstI-NcoI fragment of a PSA regulatory region.

This nucleic acid sequence of the top line of FIG. 4 contains approximately 822 bp of DNA. Generally, the PSAR sequence is from restriction sites Pst 1 to Nco I (FIG. 1). However, sequence polymorphisms may exist. Combined with either PCPSA promoter (Pang et al. (1995) supra) or additional copies of the 822 bp DNA sequence or other embodiments of PSAR, PSAR exhibits strong positive regulatory activity for transgene expression (FIGS. 2, 3, 7 and 8).

The invention also provides a method for producing a protein, comprising introducing a vector into a PSA-producing cell, the vector having a PSAR (e.g., the 822 bp DNA fragment of FIG. 4 (SEQ ID No: 3) or the PstI-NcoI fragment of a PSA regulatory region) and a gene encoding the protein, and culturing the PSA-producing cell into which the vector has been introduced under sufficient conditions so that the protein is produced.

BRIEF DESCRIPTION OF THE FIGURES

FIG. 4 is a nucleic acid sequence of the PSAR 822-bp DNA fragment (top line, SEQ ID No: 3). The nine nucleotide differences between the PSAR 822-bp fragment and positions 1067–1990 of the sequence present in GenBank (bottom line, SEQ ID No: 4) are underlined and italicized.

DETAILED DESCRIPTION OF THE INVENTION

Definitions

Figure 1:
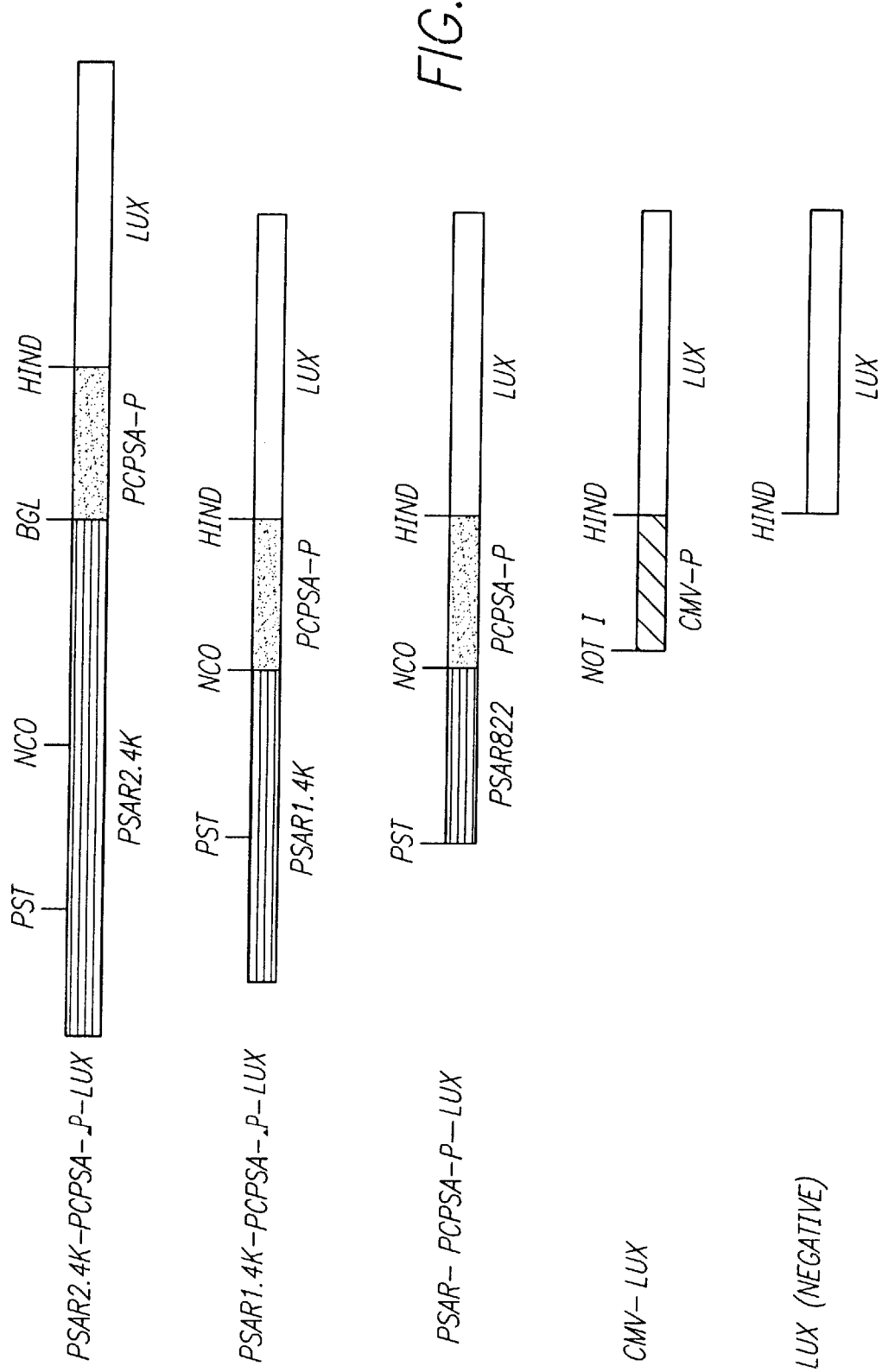
FIG. 1 is a diagram of five plasmids used for DNA transfection.

All scientific and technical terms used in this application have meanings commonly used in the art unless otherwise specified. As used in this application, the following words or phrases have the meanings specified.

As used herein "therapeutic gene" means DNA encoding an amino acid sequence corresponding to a functional protein capable of exerting a therapeutic effect on diseased or damaged cells or having a regulatory effect on the expression of a function in diseased or damaged cells.

As used herein "nucleic acid molecule" includes both DNA and RNA and, unless otherwise specified, induces both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "PSA positive regulatory sequence" (also known as PSAR) is a DNA sequence that increases gene expression in PSA-producing cells. The PSAR can be functional upstream or downstream of the gene without significant loss of activity. In one embodiment, the PSAR can increase gene expression by acting in conjunction with an additional promoter to increase the activity of the additional gene expression promoter for transcription. In another embodiment, the PEAR can increase gene expression by acting in conjunction with a second PSAR, with or without another promoter. Multiple PSARs can be used to further enhance the tissue specificity and androgen responsiveness of PSAR driven gene expression.

As used herein "PSAR regulatory activity" means ability to enhance gene expression in PSA-producing cells relative to non-PSA-producing cells and in response to stimulation with androgen, e.g. dihydrotestosterone (DHT).

As used herein "PSA regulatory region" mean, a nucleic acid sequence 5' of the coding region of the PSA gene.

As used herein "PSA promoter" means a promoter capable of increasing transcription of a gene in a PSA-producing cell. Examples of PSA promoters include, but are not limited to PCPSA promoter (Pang et al. (1995) supra), PSAP (Riegman et al. (1991) supra) and PSAR. The PCPSA promoter is disclosed in FIG. 10 of U.S. Ser. No. 08/522, 841, filed Sep. 1, 1995.

In order that the invention herein described may be more fully understood, the following detailed description is set forth.

Compositions of the Invention

The present invention provides an isolated nucleic acid molecule which is a PSA positive regulatory sequence (PSAR). This molecule has been deposited under the requirements of the Budapest Treaty on May 27, 1996 with the American Type Culture Collection ("ATCC"), 12301 Parklawn Drive, Rockville, Md. 20852 U.S.A., and has been identified as ATCC Accession No.: 97495. All restrictions imposed by the depositor on the availability to the public of the deposited material will be irrevocably removed upon the granting of a patent in this U.S. application.

In one embodiment of the invention, the molecule comprises a nucleic acid molecule shown in FIG. 4 (SEQ ID No: 3). In another embodiment of the invention, the molecule comprises a nucleic acid molecule that hybridizes with the nucleic acid sequence shown in the top line of FIG. 4 (SEQ ID No: 3), wherein the nucleic acid sequence is other than that described by Schuur et al. (1996, supra) or shown in the bottom line of FIG. 4 (SEQ ID No: 4). The hybridization is under conventional hybridization conditions, preferably under stringent conditions. In yet another embodiment, the PSAR comprises a PstI-NcoI fragment of a PSA regulatory region.

The invention also includes DNA molecules that encode anti-sense RNAs or specific ribozymes which allow the control of the expression of the nucleic acid molecules of the invention in host and target cells. The anti-sense RNAs and specific ribozymes are also included in the invention. In another embodiment, the invention relates to primer, that allow the specific amplification of nucleic acid molecules of the invention or of any specific parts thereof. In another embodiment, the invention relates to probes that specifically hybridize to nucleic acid sequences of the invention or to any part thereof.

The PSAR molecule of the invention may be inserted into a vector together with a gene of interest. The gene of interest can be a therapeutic gene. Preferably, the gene of interest is positioned downstream of the PSAR. The resulting vector is referred to herein as a genetically modified vector.

In accordance with the practice of the invention, the molecule may be combined with a PSA promoter. Preferably, the molecule is positioned 5' of the promoter in the vector.

In one embodiment, the molecule may be combined with a second molecule of the invention such that at least two PSARs are present in the vector. Multiple PSARs may be positioned adjacent to one another in the vector or with intervening sequences. Preferably, the multiple PSARs are positioned in a tandem orientation.

The nucleic acid molecule of the invention may be modified, i.e., by sequence mutations, deletions, and insertions, so as to produce functionally equivalent derivative molecules. Other modifications include multiplying the number of sequences that can bind prostate cell specific regulatory proteins, deleting of the non-functional subregions, deleting sequences that are nonfunctional in the positive regulatory sequence PSAR.

Derivative molecules would retain the functional property of the PSAR, namely, the molecule having such substitutions will still permit the enhanced expression of the gene of interest (also referred to herein as a therapeutic gene). Modification is permitted so long as the derivative molecules retain increased potency compared to PSAR alone and tissue specificity.

The invention provides a pharmaceutical composition comprising a vector, wherein the vector comprises a PSAR and a gene of interest. In one embodiment, the vector further comprises a second PSAR such that at least two PSARs are present in the vector. To enhance gene expression, multiple PSARs within the vector are possible. Preferably, the gene of interest is positioned downstream of the PSAR. One example of a gene of interest is a therapeutic gene.

The invention also provides a diagnostic composition comprising a PSA-producing cell having a vector, wherein the vector comprises a gene of interest and PSAR. Preferably, the gene of interest is positioned downstream of the PSAR. The gene of interest is selected so as to encode a product reactive with a molecule associated with a condition to be diagnosed. One example of a gene of interest is a ras gene, whose product can be used in the detection of ras antibodies in a sample for the clinical assessment of whether a subject's immune system is combating a disease associated with elevated levels of ras.

In accordance with the practice of the invention, a vector can be constructed by inserting a heterologous sequence (e.g., a therapeutic gene) into the nucleic acid molecule of the invention downstream of the PSAR.

Examples of therapeutic genes include suicide genes. These are gene sequences the expression of which produces a protein or agent that inhibits prostate tumor cell growth or kills prostate tumor cells. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill prostate cancer cells or produce cytokines or other cytotoxic agents which directly or indirectly inhibit the growth of or kill the prostate cancer cells. In one embodiment, the therapeutic gene encodes an antibody.

Suitable enzymes include thymidine kinase (TK), xanthineguanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include neu, EGF, ras (including H, K, and N ras), p53 retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); *E. coli* LT toxins, Shiga toxin, Shiga-like toxins (SLT1, -2), ricin, abrin, supporin, and gelonin.

Suitable cytokines include interferons, GM-CSF interleukins, tumor necrosis factor (TNF) (Wong, G. et al. (1985) Human GM-CSF: Molecular cloning of the complementary DNA and purification of the natural and recombinant proteins, Science 228:810); WO9323034 (1993); Horisberger, M. A. et al. (1990) Cloning and sequence analyses of cDNAs for interferon- and virus-induced human Mx proteins reveal that they contain putative guanine nucleotide-binding sites: functional study of the corresponding gene promoter, Journal of Virology 64(3):1171–81; Li, Y. P. et al. (1992) Proinflammatory cytokines tumor necrosis factor-alpha and IL-6, but not IL-1, down-regulate the osteocalcin gene promoter, Journal of Immunology 148(3):788–94; Pizarro, T. T. et al. (1993) Induction of TNF alpha and TNF beta gene expression in rat cardiac transplants during allograft rejection, Transplantation 56(2):399–404). (Breviario, F. et al. (1992) Interleukin-1-inducible genes in endothelial cells. Cloning of a new gene related to C-reactive protein and serum amyloid P component, Journal of Biological Chemistry 267(31):22190–7; Espinoza-Delgado, I. et al. (1992) Regulation of IL-2 receptor subunit genes in human monocytes. Differential effects of IL-2 and IFN-gamma, Journal of Immunology 149(9):2961–8; Algate, P. A. et al. (1994) Regulation of the interleukin-3 (IL-3) receptor by IL-3 in the fetal liver-derived FL5.12 cell line, Blood 83(9):2459–68; Cluitmans, F. H. et al. (1994) IL-4 down-regulates IL-2-, IL-3-, and GM-CSF-induced cytokine gene expression in peripheral blood monocytes, Annals of Hematology 68(6):293–8; Lagoo, A. S. et al. (1994) IL-2, IL-4, and IFN-gamma gene expression versus secretion in superantigen-activated T cells. Distinct requirement for costimulatory signals through adhesion molecules, Journal of Immunology 152(4):1641–52; Martinez, O. M. et al. (1993) IL-2 and IL-5 gene expression in response to alloantigen in liver allograft recipients and in vitro, Transplantation 55(5):1159–66; Pang, G. et al. (1994) GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha, Clinical and Experimental Immunology 96(3):437–43; Ulich, T. R. et al. (1991) Endotoxin-induced cytokine gene expression in vivo, III, IL-6 mRNA and serum protein expression and the in vivo hematologic effects of IL-6, Journal of Immunology 146(7):2316–23; Mauviel, A. et al. (1992) Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity, Journal of Immunology 149(9):2969–76).

Growth factors include transforming growth factor-α (TGFα) and β (TGFβ), cytokine colony stimulating factors (Shimane, M. et al. (1994) Molecular cloning and characterization of G-CSF induced gene cDNA, Biochemical and Biophysical Research Communications 199(1):26–32; Kay, A. B. et al. (1991) (Messenger RNA expression of the cytokine gene cluster, interleukin 3(IL-3), IL-4, IL-5, and granulocyte/macrophage colony-stimulating factor, in allergen-induced late-phase cutaneous reactions in atopic subjects, Journal of Experimental Medicine 173(3):775–8; de Wit, H. et al. (1994) Differential regulation of M-CSF and IL-6 gene expression in monocytic cells, British Journal of Haematology 86(2):259–64; Sprecher, E. et al. (1992) Detection of IL-1 beta, TNF-alpha, and IL-6 gene transcription by the polymerase chain reaction in keratinocytes, Langerhans cells and peritoneal exudate cells during infection with herpes simplex virus-1, Archives of Virology 126(1–4):253–69).

Vectors for use in the methods of the present invention include viral vectors such as adenoviruses, retroviral vectors, adeno-associated viral (AAV) vectors, a vaccinia virus vector, a herpes virus vector and a rabies virus vector. Alternatively, the vector can be a non-viral vector such as a plasmid.

The viral vector selected should meet the following criteria: (1) the vector must be able to infect the tumor cells and thus viral vectors having an appropriate host range must be selected; (2) the transferred gene should be capable of persisting and being expressed in a cell for an extended period of time; and (3) the vector should be safe to the host. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruse; Epstein-Barr Virus, (EBV); papilloma viruses, e.g. bovine papilloma virus type I (BPV); vaccinia and poliovirus and other human and animal viruses.

Adenoviruses have several properties that make them attractive as cloning vehicles (Bachettis et al. (1977) Transfer of gene for thymidine kinase-deficient human cells by purified herpes simplex viral DNA, PNAS U.S.A. 74:1590; Berkner, K. L. (1988) Development of adenovirus vectors for expression of heterologous genes, Biotechniques 6:616; Ghosh-Choudhury, G. et al. (1986) Human adenovirus cloning vectors based on infectious bacterial plasmids, Gene 50:161; Hag-Ahmand, Y. et al. (1986) Development of a helper-independent human adenovirus vector and its use in the transfer of the herpes simplex virus thymidine kinase gene, J. Virol. 57:257; Rosenfeld, M. et al. (1991) Adenovirus-mediated transfer of a recombinant α$_1$-antitrypsin gene to the lung epithelium in vivo, Science 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb Df heterologous sequences for native adenovirus sequences generating viable, conditional, helper-independent vectors (Kaufman, R. J. (1985) Identification of the component necessary for adenovirus translational control and their utilization in cDNA expression vectors, PNAS U.S.A. 82:689).

AAV is a small human parvovirus with a single stranded DNA genome of approximately 5 kb. This virus can be propagated as an integrated provirus in several human cell types. AAV vectors have several advantages for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. (1990) An efficient deletion mutant packaging system for a defective herpes simplex virus vectors: Potential applications to human gene therapy and neuronal physiology, Proc. Natl. Acad. Sci. U.S.A. 87:8950).

Another vector for mammalian gene transfer is the bovine papilloma virus-based vector (Sarver, N. et al. (1981) Bovine papilloma virus DNA: A novel eukaryotic cloning vector, Mol. Cell Biol. 1:486).

Vaccinia and other poxvirus-based vectors provide a mammalian gene transfer system. Vaccinia virus is a large double-stranded DNA virus of 120 kilodaltons (kd) genomic size (Panicali, D. et al. (1982) Construction of poxvirus as cloning vectors: Insertion of the thymidine kinase gene from herpes simplex virus into the DNA of infectious vaccine virus, Proc. Natl. Acad. Sci. U.S.A. 79:4927; Smith, et al. (1983) Infectious vaccinia virus recombinants that express hepatitis B virus surface antigens, Nature 302:490.)

Retroviruses are packages designed to insert viral genes into host cells (Guild, B. et al. (1988) Development of retrovirus vectors useful for expressing genes in cultured murine embryonic cells and hematopoietic cells in vivo, J. Virol. 62:795; Hock, R. A. et al. (1986) Retrovirus mediated transfer and expression of drug resistance genes in human hemopoietic progenitor cells, Nature 320:275).

The basic retrovirus consists of two identical strands of RNA packaged in a proviral protein. The core surrounded by a protective coat called the envelope, which is derived from the membrane of the previous host but modified with glycoproteins contributed by the virus.

The invention also provides a host vector system comprising a vector of the invention in a suitable host cell. Examples of a suitable host cell include, but are not limited to, bacterial cells and eucaryotic cells. Examples of a eucaryotic host cell include, but are not limited to, a PSA-producing cell, an animal cell and a human cell.

Methods of the Invention

This invention involves targeting a gene of interest to the diseased site so that the protein encoded by the gene is expressed and directly or indirectly ameliorates the diseased state.

After infecting a susceptible cell, the therapeutic gene driven by a specific promoter in the vector expresses the protein encoded by the gene. The use of PSAR will allow enhanced expression of the specific genes in cancer or diseased cells.

In one embodiment, the present invention relates to a process for administering modified vectors into the prostate to treat prostate cancer or disorders associated with the prostate. More particularly, the invention relates to the use of vectors having PSAR and functional therapeutic genes to produce molecules that are capable of directly or indirectly affecting cells in the prostate to repair damage sustained by the cells from defects, disease or trauma. In one embodiment, the vector further comprises a second PSAR. Multiple PSARs can be used to further enhance the tissue specificity and androgen responsiveness of PSAR driven gene expression.

Preferably, for treating defects, disease or damage of cells in the prostate, vectors of the invention include a therapeutic gene, in the form of a transgene, e.g., a gene encoding TK, a promoter and PSAR. Alternatively, vectors of the invention include a therapeutic gene in the form of a transgene, two or more PSARs and, optionally, another promoter. The genetically modified vectors are administered into the prostate to treat defects or disease, such as prostate cancer, by introducing a therapeutic gene product or products into the prostate that have ameliorative effects in vivo.

The basic tasks in the present method of the invention are isolating the gene of interest, selecting the proper vector vehicle to deliver the gene of interest to the body, administering the vector having the gene of interest into the body, and expressing the gene of interest. In a preferred embodiment, the vector is an adenoviral vector, which is preferably administered directly into the body without packaging of the virus. In another embodiment, the vector is a retroviral vector, which is preferably administered within a packaging cell. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

Along with the human or animal gene of interest, another gene, e.g., a selectable marker, can be inserted that will allow easy identification of cells that have incorporated the vector. The critical focus on the process of gene therapy is that the new gene must be expressed in target cells at an appropriate level with a satisfactory duration of expression.

In addition, the invention provides a method for producing a protein comprising introducing a vector into a PSA-producing cell. The vector comprises a PstI-NcoI fragment of a PSA regulatory region and a gene encoding the protein. The method further comprises culturing the PSA-producing cell into which the vector has been introduced so as to produce the protein and recovering the protein so produced. The culturing can be in vitro or in vivo. The PstI-NcoI fragment of the PSA regulatory region may be the 822-bp fragment shown in the top line of FIG. 4 (SEQ ID No: 3), a derivative thereof, the 824-bp fragment shown in the bottom line of FIG. 4 (SEQ ID No: 4) or a derivative thereof so long as the fragment retains the positive regulatory activity of PSAR. The PstI-NcoI fragment of the PSA regulatory region can be present as two or more copies in the vector. In other PSA promoter sequences, there will be PstI-NcoI fragments that do not necessarily have a nucleic acid sequence identical to that of FIG. 4 (SEQ ID No: 3), i.e. sequence polymorphisms that can exist between species and among members thereof. This method for producing a protein allows for enhancing expression of the protein by stimulation with androgen, e.g. DHT.

In one embodiment, the invention provides a method for producing a protein comprising culturing a host vector system of the invention so as to produce the protein encoded by the gene in the host.

In one embodiment, the gene is a suicide gene such as thymidine kinase. In one embodiment, the protein is a tumor suppressor gene. In another embodiment, the protein is a growth factor. In another embodiment, the protein is a toxin. In another embodiment, the protein is an antibody. In another embodiment, the protein is a cytokine. Examples of a cytokine include, but are not limited to, an interferon, a colony stimulating factor, a granulocyte colony stimulating factor and a granulocyte macrophage colony stimulating factor.

The methods described below to modify vectors and administer such modified vectors into the prostate are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, or convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., (1982) in Molecular Cloning: A Laboratory Manual, Cold Spring Harbor Laboratory, New York). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g., New England Biolabs Product Catalog). In general, about 1 $\mu$g of plasmid or DNA sequence is cleaved by one unit of enzyme in about 20 $\mu$l of buffer solution. Typically, an excess of restriction enzyme is used to insure complete digestion of the DNA substrate.

Incubation times of about one hour to two hours at about 37° C. are workable, although variations can be tolerated. After each incubation, protein is removed by Extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980).

Restriction cleaved fragments may be blunt ended by treating with the large fragment of *E. coli* DNA polymerase I (Klenow) in the presence of the four deoxynucleotid triphosphates (dNTPs) using incubation times of about 15 to 25 min at 20° C. to 25° C. in 50 mM Tris (pH 7.6) 50 mM NaCl, 6 mM $MgCl_2$, 6 mM DTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 μl volumes under the following standard conditions and temperatures using T4 DNA ligase. Ligation protocols are standard (D. Goeddel (ed.) Gene Expression Technology: Methods in Enzymology (1991)).

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman (1991), Vectors used for expression in mammalian cells, in Gene Expression Technology, edited by D. V. Goeddel.

Many methods for inserting functional DNA transgenes into cells are known in the art. For example, non-vector methods include nonviral physical transfection of DNA into cells; for example, microinjection (DePamphilis et al. (1988) BioTechnique 6:662–680; Felgner et al. (1937) Liposomal mediated transfection, Proc. Natl. Acad. Sci. U.S.A., 84:7413–7417; Felgner and Holm (1989) Focus 11:21–25 and Felgner et al. (1989) Proc. West. Pharmacol. Soc. 32:115–121) and other methods known in the art.

Administration of Vectors into Subject

Before administration, the modified vectors ire suspended in complete PBS at a selected density for injection. Examples of a density that may be selected for injection (e.g., using an adenoviral vector) include, but are not limited to, $10^8$–$10^{10}$ plaque forming units (pfu) in 100 μl of solution. Preferably, the density for injection is $10^9$ pfu in 100 μl of solution. The volume of solution can be varied in accordance with the size of the tumor to be infected. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the prostate, is relatively non-traumatic, allows multiple administrations simultaneously in several different sites or the same site using the same viral suspension. Multiple injections may consist of a mixture of therapeutic genes. Ex vivo administration is possible.

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J C, et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the prostate cells.

The spheroplasts are maintained in high ionic strength buffer until they can be fused through the mammalian target cell using fusogens such as polyethylene glycol (PEG).

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji, et al. (1981) Cell 27:299; Corden et al. (1980) Science 209:1406; and Breathnach and Chambon (1981) Ann. Rev. Biochem. 50:349).

For retroviruses, control elements involved in the replication of the retroviral genome reside in the long terminal repeat (LTR) (Weiss et al., eds., (1982), In: The molecular biology of tumor viruses: RNA tumor viruses, Cold Spring Harbor Laboratory, Cold Spring Harbor, N.Y.

Moloney murine leukemia virus (MLV) and Rous sarcoma virus (RSV) LTRs contain promoter and enhancer sequences (Jolly et al. (1983) Nucleic Acids Res. 11:1855; Capecchi et al. In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al. (1985) Nature 314:285; Rossi and de Crombrugghe, Proc. Natl. Acad. Sci. U.S.A. 84:5590–5594).

In a first embodiment, the invention provides a method for producing a protein product comprising culturing the host vector system of the invention so as to produce the protein in the host and recovering the protein so produced. This method permits the expression of genes of interest in both unicellular and multicellular organisms. For example, in an in vitro assay, prostate cells having the vector comprising a gene of interest (e.g., the ras gene) and PSAR may be used in microtiter wells as an unlimited source for the ras gene product. A sample from a subject would be added to the wells to detect the presence of antibodies directed against the ras gene. This assay can aid in the quantitative and qualitative determination of the presence of ras antibodies in the sample for the clinical assessment of whether the subject's immune system is combatting the disease associated with elevated levels of ras.

In a second embodiment, prostate cancer is treated via gene therapy, i.e., the correction of a disease phenotype in vivo through the use of the nucleic acid molecules of the invention. The treatment can be directed to metastatic, androgen-independent or PSA-producing prostate cancers.

In accordance with the practice of this invention, the subject of the gene therapy may be a human, equine, porcine, bovine, murine, canine, feline, or avian subject. Other warm blooded animals are also included in this invention.

The most effective mode of administration and dosage regimen for the molecules of the present invention depends upon the exact location of the prostate tumor being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m² of surface area is described by Freireich, E. J. et al. (1966) Cancer Chemother. Rep. 50(4):219–244. Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation).

Advantages of the Invention

The PSAR sequence of the invention increases gene expression by more than 1000-fold in PSA-producing prostate cells, but does not increase the expression of the transgene in non-PSA-producing cells. This tissue specificity is useful for developing prostate-tissue specific gene delivery vectors.

The PSAR sequence of the invention shows responsiveness to androgen stimulation. The activity can be increased to more than 1000-fold higher with the addition of androgen, e.g. dihydrotestosterone (DHT), 10–100 nM. This property is useful to adjust the PSAR activity, specifically in treatment of patients.

A vector having two PSAR fragments shows enhanced promoter activity compared to a vector having one PSAR sequence together with a PCPSA-P expression promoter. PSAR activity, androgen sensitivity and tissue specificity can be enhanced by increasing the number of PSAR sequences present in a vector.

In one embodiment, the PSAR comprises 822 bp. The size can be cut even shorter to maintain its function. Combined with the PCPSA promoter from Bgl II site to Hind III site (~550 bp) a complete functional sequence is approximately 1.4 kb. The size of 1.4 kb can be easily cloned into various viral or non-viral vectors to drive therapeutic genes.

The PstI-NcoI fragment of the invention offers several advantages over the molecules published recently by Schuur et al. (1996, supra). Their results documented that the 5' region from XbaI to PstI is essential to maintain the positive regulatory activity. In contrast, the data herein demonstrate that the deletion of this region does not decrease the expression of the transgene. We also noticed a different responsiveness to androgen stimulation in LNCaP cells. With the addition of androgen, an activity increase of more than 1000-fold was observed.

This increase in activity is significantly higher than that observed by Schuur's group. The promoter sequence herein was derived from fresh prostatic tumor of a patient with advanced prostate cancer that expressed high PSA levels. In contrast, Schuur et al. derived their promoter sequence from peripheral blood cells of an unidentified patient. There are nine nucleotide differences between the 822 bp DNA sequence herein and Schuur's sequence, and the one at position 625 T appears to be important for enhancer activity (el-Shirbiny, A. M. (1994) Prostatic specific antigen, Adv. Clin. Chem. 31:99–133). We speculate that our sequence has a higher binding affinity for the androgen receptor because the similarity to the identified androgen-responsive element of our element is higher.

A 5' 570-bp sequence is disclosed in Schuur's clone which contains a functional domain. In the isolated fragment disclosed herein, the mutations in the 822-bp region greatly increase the positive regulatory activity, and the 5' 570 bp is no longer needed.

In order that the invention described herein may be more fully understood, the following examples are set forth. It should be understood that these examples are for illustrative purposes only and are not to be construed as limiting the scope of this invention in any manner.

EXAMPLE 1

This example describes the identification of a positive regulatory element (PSAR) responsible for tissue-specific expression of prostate-specific antigen.

Materials and Methods

PCR Cloning and Construction of Plasmids

Using our PSA promoter sequence as the probe, we searched Genbank and found a 5.8 kb DNA sequence of Locus HSU376721 upstream of the PSA gene submitted by Schuur and coworkers (Shuur, E. R. et al. (1995) supra; Genbank Accession No. U37672). The 3' sequence that contains PSA promoter has been characterized by several research groups so we focused on the 5' half of this 5.8 kb DNA (Riegman P. H. et al. (1991) supra).

PCR primers were designed to amplify sequences from nucleotide (nt) 503 to nucleotide 2950 of the GenBank sequence (Shuur, E. R. et al. (1995) supra). DNA isolated from a patient with advanced prostate cancer was used as the template (Pang S., et al. (1995) supra).

A DNA fragment of ≈2.4 kb was obtained using PCR primers with sequences of CTTTT AGTAT GCGGC CGCTC TAGAA ATC (SEQ ID No: 1) and CCTGG GTAGT CCTTT TACAA GATCT GGTGG AG (SEQ ID No: 2). This DNA fragment was inserted into a plasmid containing PCPSA promoter and luciferase gene in pUCBM20 (Riegman P. H., et al. (1991) supra). The plasmid containing ≈2.4 kb DNA fragment was further digested using restriction endonucleases to remove an approximately 1 kb DNA fragment from the 3' end. The 1.4 kb fragment was further digested by restriction enzymes to remove the 5' ≈570 bp DNA sequence to generate a fragment of ≈820 bp. Both the ≈1.4 kb and ≈820 bp DNA fragments were also cloned into the pUCEM20-PCPSA-P-Lux plasmid (FIG. 1). The positive control plasmid contains the immediate early gene promoter of cytomegalovirus (the CMV promoter), whereas the negative control plasmid contains no promoter.

The PCPSA promoter is a DNA fragment upstream of PSA gene isolated from a patient with advanced prostate cancer. The sequence is from restriction endonucleases Bgl II to Hind III and approximately 550 bp has been used to construct the plasmid PSAR-PCPSA-P-Lux.

Tumor Cell Line Culture and Maintenance

The culture of cell lines LNCaP, PC-3 and R11 has been described previously (Pang et al. (1995) supra). HeLa cells were cultured according to the conditions suggested by American Type Culture Collection (ATCC). Cells subjected to androgen stimulation tests were maintained in media with 10% CFBS 2 days before DNA transfection. To prepare CFBS, charcoal (0.625 g; Mallinckrodt) and 12.5 mg of dextran sulfate were washed with 500 ml of PBS once before being mixed by shaking or Vortex for 30 minutes with 500 ml of FBS. The charcoal was removed from the serum by centrifugation at 1500×g, followed by 0.2-μm filtration.

DNA Transfections and Luciferase Assay

Several transfection methods were tested and both lipofection and electroporation efficiently introduce the plasmids with newly cloned DNA fragments into tumor cell lines.

Plasmids containing 2.4 kb and 1.4 kb PSA regulatory DNA fragments were used to transfect PSA-producing prostate cell line LNCaP, liver cell line HEPG2, breast cancer cell line MCF-7 and renal cell line R11 using lipofection. For lipofection, liposomes 10 μl of 0.747 mM DRMIE/ DOPE (1:1) provided by Vical (San Diego) were mixed with five μg of plasmid DNA in 1 ml RPMI 1640 (GIBCO-BRL) medium before applying to cells in 6-well plates. Four hours post transfection, an additional 0.5 ml of medium with 30% heat inactivated fetal bovine serum were added. Cells were lysed approximately two days post transfection using lysis buffer purchased from Promega (Madison, Wis.) followed by luciferase assay.

For electroporation, cells were trypsinized from T175 flasks and washed twice using electroporation medium (1.2× RPMI with 10% fetal bovine serum). The cells were resuspended in electroporation medium at $2 \times 10^7$ cells/ml. Cell suspensions of 0.25 ml were mixed with 10 μg DNA in ice for 10 minutes before electroporation. The cells were pulsed at 230 volts with 960 μF using a Bio-Rad Gene Pulser (Bio-Rad, Hercules, Calif.). The treated cells were kept in ice for another 10 minutes before replating. At 16 hours, the plates were washed with serum free medium once before adding new culture medium. Cells were collected approximately 48 hours after transfection with 1× tissue lysis buffer. Firefly luciferase activity of the cell lysates was measured by luminometry. For each assay, 10 μl of cell lysate was used. The protein amount of 10 μl cell lysate was measured using a Bio-Rad kit. The luciferase activity was finally adjusted in accordance with the concentration of protein in cell lysates.

In order to identify the essential region responsible for regulating the PSA gene expression specificity, we introduced an additional deletion to remove the 5' end ≈570 bp from the Xba I to Pst I sites (FIG. 1). Cell lines were maintained in RPMI medium supplemented with 10% charcoal stripped fetal bovine serum for two days (Pang S, et al. (1995) supra). Equal amounts of plasmid DNAs were used for electroporation. The transfected cells were plated into 6-well culture plates and DHT was added to concentrations of 0, 10 and 100 nM. Two days posttransfection, cells were collected for luciferase assay.

Results

Tissue Specificity and Androgen Response of the Cloned PSA Regulatory Sequences

PSA gene expression was characterized by its tissue specificity and androgen responsiveness (Hara, M. and Kimura, H. (1989) Two prostate-specific antigens, γ-seminoprotein and β-microseminoprotein, J. Lab. Clin. Med. 113:541–548; Wang, M. C. et al. (1979) Purification of a human prostate specific antigen, Invest. Urol. 17:159–163; Chan, D. W. et al. (1987) Prostate-specific antigen as a marker for prostatic cancer: a monoclonal and a polyclonal immunoassay compared, Clin. Chem. 33:1916–1920; Emtage, L. A. et al. (1987) The role of prostate specific antigen in the baseline assessment of patients undergoing hormone therapy for advanced prostate cancer, Br. J. Urol. 60:572–577; Riegman, P. H. et al. (1991) The promoter of the prostate-specific antigen gene contains a functional androgen responsive element, Mol. Endocrinal. 5:1921–1930; el-Shirbiny, A. M. (1994) Prostatic specific antigen, Adv. Clin. Chem. 31:99–133; Wolf, D. et al. (1992) Transcriptional regulation of prostate kallikrein-like genes by androgen, Mol. Endocrinal. 6:753–762).

Figure 2:
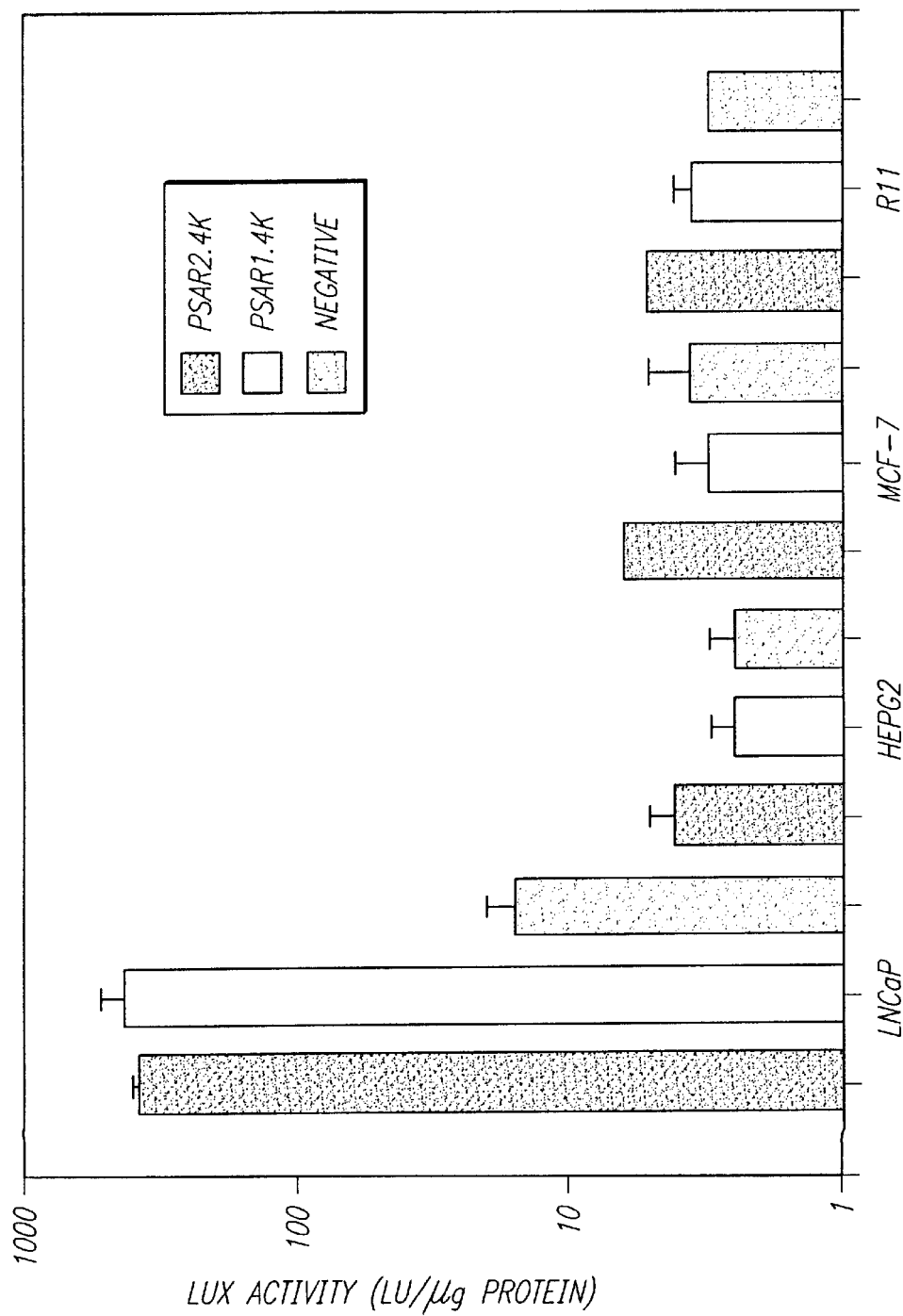
FIG. 2 is a bar graph demonstrating the luciferase gene expression in transfected cell lines LNCaP, MCF-7, HEPG2 and R11.

The plasmids containing 2.4 kb and 1.4 kb DNP fragments were lipofected into PSA-producing prostate cell line LNCaP and non-prostate cell lines R11, MCF-7 and HEP-G2. Detectable androgen receptor mRNA is present in both LNCaP and MCF-7 cell lines, while the other cells produce neither PSA protein nor androgen receptor (FIG. 2). A plasmid containing only a luciferase gene with no promoter was used as the negative control. The scale of luciferase activity shown in FIG. 2 is in a logarithmic format, therefore the activity of PSAR sequences were ≈30-fold higher in LNCaP cells than in the negative control. PSAR sequences showed no activity in other cells.

In all tested cell lines, PSA regulatory sequences of 2.4 kb and 1.4 kb lengths showed no significant difference. In LNCaP cells, the fragment of 1.4 kb demonstrated a 10–30% higher activity compared with the 2.4 kb fragment. In the control cell lines, both fragments demonstrated essentially identical activity, comparable to the negative control plasmid containing no promoter (FIG. 2).

Although MCF-7 cell line produces detectable androgen receptor (AR), both plasmids, containing 2.4 kb or 1.4 kb regulatory fragments and PCPSA promoter, did not show significant increase of luciferase gene expression compared with the negative control. This suggests that the control mechanism involves prostate tissue specific factors found only in PSA-producing prostate cells.

Figure 3A:
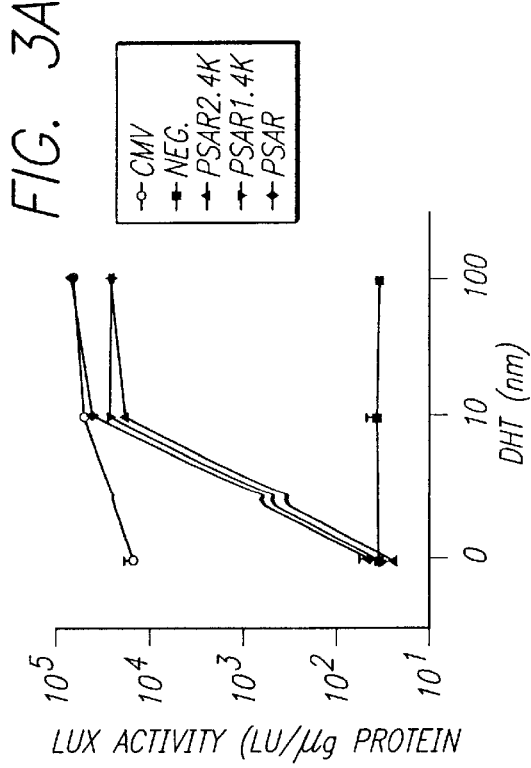
FIG. 3A is a line graph showing luciferase activity in LNCaP cells transfected by electroporation with CMV promoter (○), no promoter (■), PSAR2.4 kb-PCPSA-P (▲), PSAR1.4 kb-PCPSA-P (▼), or 822 bp PSAR-PCPSA-P (♦), and grown in varying concentrations of DHT.
Figure 3B:
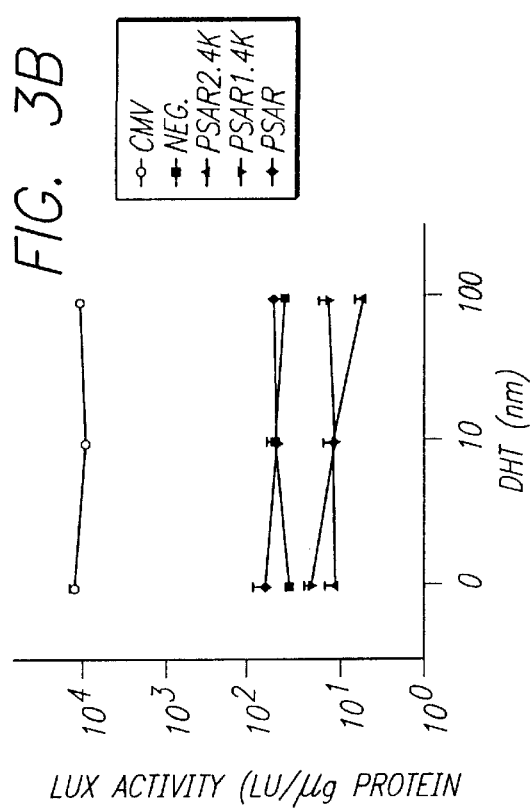
FIG. 3B is a line graph showing luciferase activity in PC-3 cells transfected by electroporation with CMV promoter (○), no promoter (■), PSAR2.4 kb-PCPSA-P (▲), PSAR1.4 kb-PCPSA-P (▼), or 822 bp PSAP-PCPSA-P (♦), and grown in varying concentrations of DHT.
Figure 3C:
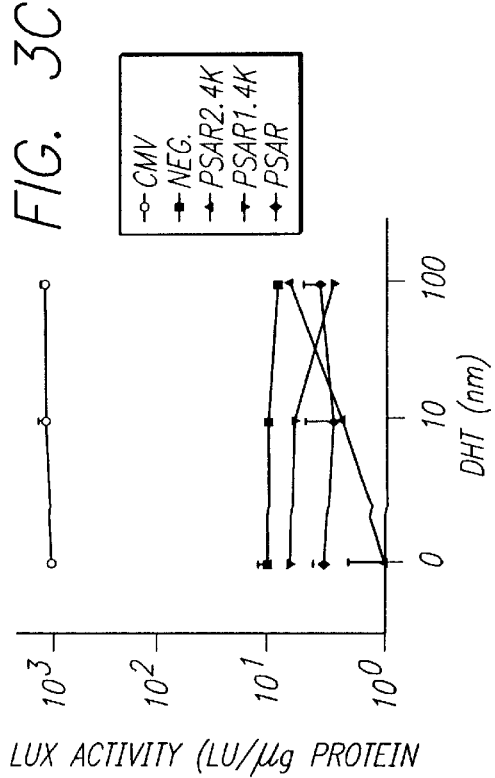
FIG. 3C is a line graph showing luciferase activity in R11 cells transfected by electroporation with CMV promoter (○), no promoter (■), PSAR2.4 kb-PCPSA-P (▲), PSAR1.4 kb-PCPSA-P (▼), or 822 bp PSAR-PCPSA-P (♦), and grown in varying concentrations of DHT.
Figure 3D:
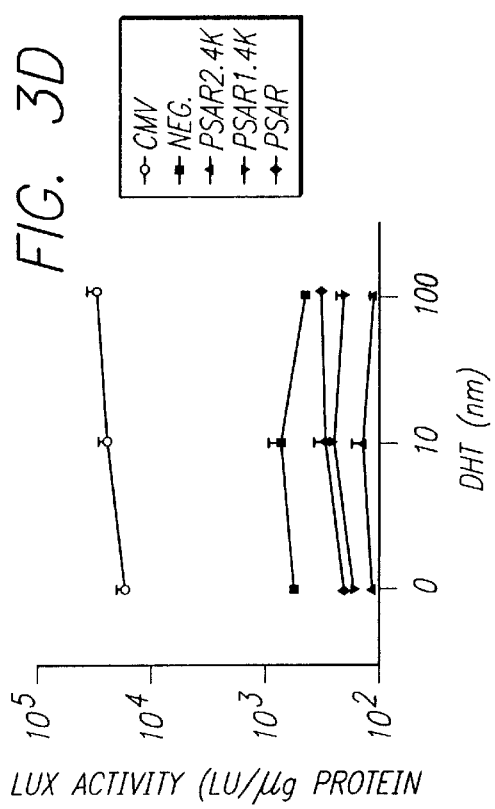
FIG. 3D is a line graph showing luciferase activity in HeLa cells transfected by electroporation with CMV promoter (○), no promoter (■), PSAR2.4 kb-PCPSA-P (▲), PSAR1.4 kb-PCPSA-P (▼), or 822 bp PSAR-PCPSA-P (♦), and grown in varying concentrations of DHT.

In electroporation studies, the negative control plasmid showed very low activity and did not respond to DHT stimulation in any of the tested cell lines. The CMV promoter showed high activity (FIGS. 3A–D) in all tested cell lines. In LNCaP cells, the CMV promoter activity increased by 3- to 4-fold with the addition of DHT (10 to 100 nM; FIG. 3A). In cell lines PC-3 and R11, the CMV promoter did not show any increase with the addition of androgen (FIGS. 3B–C). In the same transfection conditions, plasmids containing 2.4 kb, 1.4 kb and 822 bp DNA fragments showed the following expression profile in LNCaP cells. The promoter activity was very low and even lower than the negative control when no androgen was added. With the addition of DHT, the expressional activity rapidly increased more than 1000-fold. In other cell lines, the activity of PSAR 2.4 kb, 1.4 kb and 822 bp DNA fragments did not show any difference compared with the negative control, and the addition of androgen showed no effect.

This lack of response to added DHT may have teen due to the lack of androgen receptors in the PC-3 and R11 cells. To determine whether the increase in transgene expression in the LNCaP cells and the lack of expression in the PC-3 and R11 cells was due primarily to the presence of functional androgen receptors, we also transfected HeLa cells with the 2.4-kb, 1.4-kb and 822-bp DNA fragments. In our previous experiments, HeLa cells were found to possess functional androgen receptors. DHT was similarly added to the transfected HeLa cells. With the addition of DHT, the CMV promoter showed a 3- to 4-fold increased activity, similar to the LNCaP cell line. This increase may be attributed to an indirect control pathway. Androgen stimulation may activate some cellular factors that are required for CMV promoter. However, the 2.4 kb, 1.4 kb and 822 bp regulatory sequences did not show any function in HeLa cells, suggesting that other tissue-specific factors other than androgen receptors are required for the activation of the regulatory sequences.

In non-PSA-producing cell lines R11 and PC-3, the CMV promoter did not show any response to androgen stimulation (FIGS. 3B–C). This suggests that the 3- to 4-fold stimulation by androgen may result from the presence of androgen receptors in both LNCaP and HeLa cell lines. In cell lines R11 and PC-3, the luciferase gene driven by the PSA regulatory fragments and the PSA promoter does not exhibit significant reporter-gene expression compared with the negative control plasmid. The PSAP2.4-kb fragment showed a slight androgen response in PC-3 cells; however, this may be due to limitations of the luciferase assay. The sensitivity of luciferase assays is around 300 light units. Any results around 300 light units or lower are not accurate. Because the PSAR1.4-kb and the PSAR822-bp fragments did not show any response to androgen stimulation, it is more likely that the expression increase of the PSAR2.4-kb fragment stimulated with androgen was because of the limited sensitivity of luciferase assays.

Localization of the Essential Sequence

The 2.4-kb DNA fragment was digested using restriction endonucleases. The 3' ≈1-kb fragment was cleaved, resulting in a 1.4-kb DNA fragment. The 1.4-kb fragment was further digested. Its 5' ≈570 bp were cleaved, resulting in an 822-bp fragment. Comparison of the 2.4-, 1.4- and 822-bp fragments reveals that the 822-bp fragment confers a similar or higher activity of gene expression as compared to the 2.4- and 1.4 kb fragments. These findings suggest that the 822-bp fragment possesses the essential co-regulatory sequence.

Promoter Function of the Cloned PSAR 822 bp Fragment

To assess whether this cloned sequence is an enhancer or potentially a distal promoter as well, we reversed the orientation of our 1.4-kb fragment and noted that the transcriptional activity of the reversed orientation was almost identical to the activity of the plasmids containing the 1.4-kb sequence in the original orientation. The orientation-dependent property of the 1.4-kb fragment suggested that the 5' upstream sequence is not an enhancer.

Figure 5A:
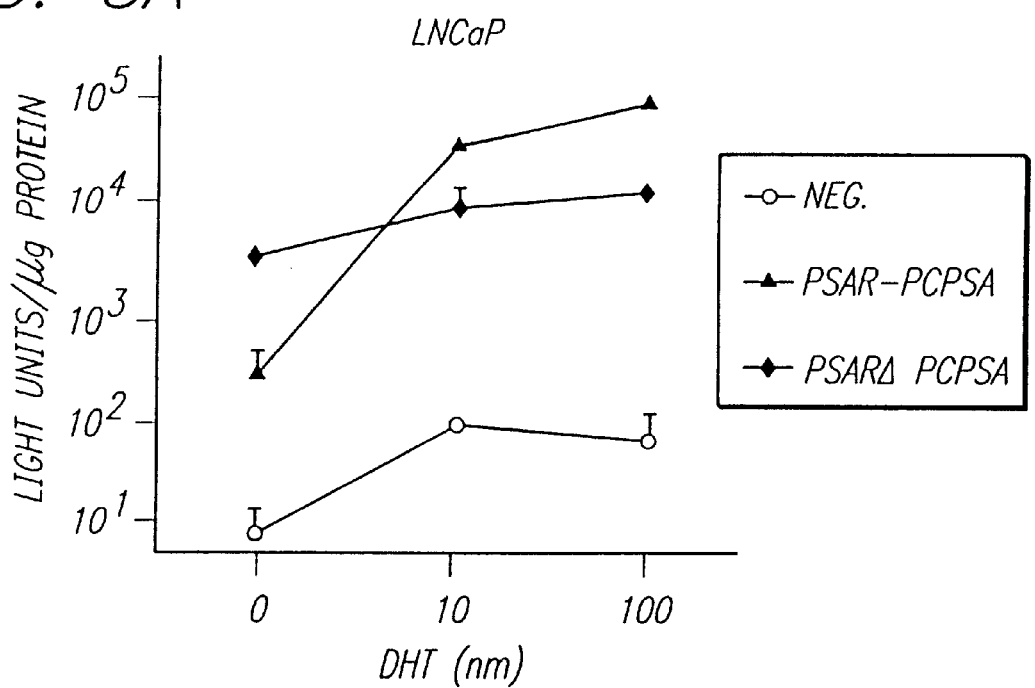
FIG. 5A is a line graph showing promoter activity and androgen responsiveness of the PSAR 822-bp fragment in LNCaP cells.
Figure 5B:
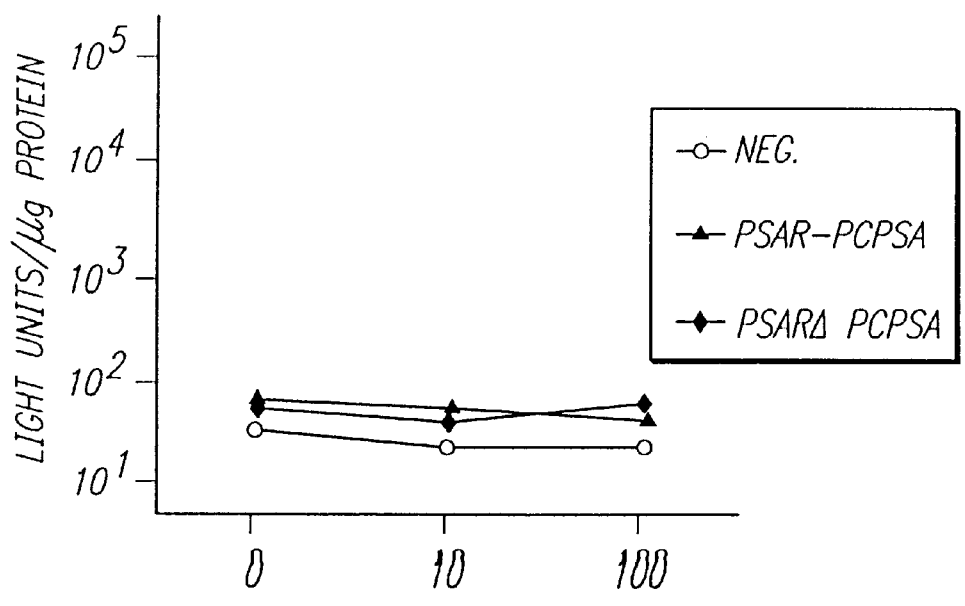
FIG. 5B is a line graph showing promoter activity and androgen responsiveness of the PSAR 822-bp fragment in HeLa cells.

Sequence analysis revealed that there is a potential TATA box for RNA transcription in the 822-bp fragment starting at position 672 (FIG. 4). This finding suggests that the 822-bp fragment may also serve as a distal promoter. To detect promoter activity of our 822-bp fragment, we deleted the PCPSA promoter from our plasmid PSAR 822-PCPSA-P-Lux, as shown in FIG. 1. The PSA promoter-deleted plasmid, the parental plasmid PSAR822-PCPSA-P-Lux, and the negative control plasmid were transfected into the LNCaP cell line and control HeLa cell line. Our results demonstrate that the sequence alone can significantly activate the expression of the transgene. Compared with the negative control, the expression level is approximately 100-fold higher in the LNCaP cell line (FIGS. 5A–B). In the HeLa control cell line, the expression of the luciferase gene driven by the 822-bp fragment did not show a significant difference compared with the negative control plasmid. Although the androgen receptor is present in HeLa cells, the promoter activity of the 822 bp did not respond to the addition of DHT. This significant increase of transgene expression indicates that the positive regulatory sequence possesses promoter function, and the promoter activity is tissue specific and androgen dependent.

The expression profile of the PSA promoter-deleted plasmid is significantly different from its parental plasmid. With no androgen added, the expression level was significantly higher. However, when DHT of 10–100 nM was added, the expression of the luciferase gene increased by only 4- to 5-fold. In comparison, the parental plasmid showed an ≈1000-fold increase. These results suggest that, in vivo, the PSA promoter may be important to maintain both high expressional activity and high androgen responsiveness for the expression of the PSA gene.

Sequencing the 822-bp PSAR Regulatory Element

The PSAR 822 bp was sequenced using a USB sequencing kit (United States Biochemical Corp., Cleveland, Ohio). Compared with the Genbank sequence HSU37672, nine nucleotide changes were noted (FIG. 4). A sequence GGAA-CAtatTGTATT was found at position 611 to 625 of the 822-bp fragment (SEQ ID No: 3). This sequence is very similar to the androgen-responsive element found in the PCPSA promoter (AGAACAgcaAGTACT, position 440–454; Pang et al. (1995) supra). The 822 bp fragment is 2 bp shorter than the corresponding region of Schuur's sequence (see dashes between positions 771 and 772 in the top line of FIG. 4).

Discussion

The use of a tissue specific promoter to drive therapeutic gene expression in target cells is a novel approach for target-specific gene therapy (Vile, R. G. and Hart, I. R. (1994) Targeting of cytokine gene expression to malignant melanoma cells using tissue specific promoter sequences, Ann. Oncol. 5 (Suppl. 4):59–65; Vile, R. G. et al. (1994) Systemic gene therapy of murine melanoma using tissue specific expression of the HSVtk gene involves an immune component, Cancer Res. 54:6228–6234; Hafenrichter, D. G. et al. (1994) Liver-directed gene therapy: evaluation of liver specific promoter elements, J. Surg. Res. 56:510–517; Cook, R. F. et al. (1993) Liver-specific expression of a phospho-henolpyruvate carboxykinase-neo gene in genetically modified chickens, Poultry Sci. 72:554–567; Hart, I. R. (1996) Tissue specific promoters in targeting systemically delivered gene therapy, Semin. Oncol. 23:154–158). Our newly identified PSA regulatory DNA fragment possesses tissue specificity and androgen sensitivity, rendering this particular regulatory fragment promising for use in gene therapy of prostate cancer.

The DNA sequence upstream of the PSA gene promoter was characterized as an enhancer by Schuur and his colleagues (Shuur, E. R. et al. (1996) Prostate specific antigen expression is regulated by an upstream enhancer, J. Biol. Chem. 271:7043–7051). The data presented herein, however, show that PSAR performs promoter functions as well as enhancer functions. PSAR alone demonstrated a 100-fold increase in transgenic expression. The PSAR sequence alone also responded to androgen stimulation; although compared with the PSAR-PCPSA-P combined promoter, both the promoter activity and the androgen responsiveness of PSAR are much lower.

Fundamental differences were observed between our results and those published recently by Schuur et al. (1996, supra). Their results documented that the 5' region from XbaI to PstI sites is essential to maintain the positive regulatory activity. In contrast, our data demonstrate that the deletion of this region does not decrease the expression of the transgene (FIG. 3). We also noticed a different responsiveness to androgen stimulation in LNCaP cells. With the addition of androgen, an activity increase of more than 1000-fold was observed.

This increase in activity is significantly higher than that observed by Schuur's group. These differences in results may be attributed to several points. First, our promoter sequence was derived from fresh prostatic tumor of a patient with advanced prostate cancer that expressed high PSA levels. In contrast, Schuur et al. derived their promoter sequence from peripheral blood cells of an unidentified patient. Second, there are nine nucleotide differences between our sequence and Schuur's sequence, and the one at position 625 T appears to be important for enhancer activity (el-Shirbiny, A. M. (1994) Prostatic specific antigen, Adv. Clin. Chem. 31:99–133). We speculate that our sequence has a higher binding affinity for the androgen receptor because the similarity to the identified androgen-responsive element of our element is higher.

We hypothesize that the 5' 570-bp sequence that is essential in Schuur's clone contains a functional domain. This functional domain is normally required to maintain the positive regulatory function. In our isolated fragment, the mutations in the 822-bp region greatly increase the positive regulatory activity, and the 5' 570 bp is no longer needed. A similar finding was also demonstrated for the PSA promoter. Schuur's PSA promoter alone did not show any transcriptional increase, but our PSA promoter showed significant transcriptional increase (Pang et al. (1995) supra; Schuur et al. (1996) supra).

The ≈820 bp sequence of the invention showed high tissue-specificity to PSA-producing prostate cells. We tested PSA-producing cell line LNCaP and other non-PSA-producing cell lines, including HEPG2 liver cell line, MCF-7 breast cancer cell line, R11 renal tumor cell line, PC-3 prostate cell line and HeLa epithelioid carcinoma cell line. PSAR sequence showed very high activity only in the LNCaP cell line.

The high potency of the PSAR-PCPSA-P promoter-enhancer sequence suggests that generating an androgen-responsive, tissue-specific vector system with high efficacy is feasible. Furthermore, the combined PSAR-PCPSA-P promoter with a ≈1.4 kb size can be easily cloned into adenoviral, retroviral, or adeno-associated viral vectors without associated packaging difficulties. With the addition of therapeutic genes such as cytotoxic genes (e.g., thymidine kinase gene) cytokine genes (e.g., interleukin 2 gene or interferon α gene), or tumor suppressor genes (e.g., p53 gene), the vector can be used for prostate cancer gene therapy or for benign prostatic hyperplasia (BPH) gene therapy.

EXAMPLE 2

This example describes increasing PSAR tissue specificity and androgen responsiveness with an additional PSAR DNA fragment. The example further shows that increased tissue specificity and androgen responsiveness can be achieved without using PCPSA promoter.

Materials and Methods

Construction of Plasmid Containing Two PSAR Sequences

Figure 6:
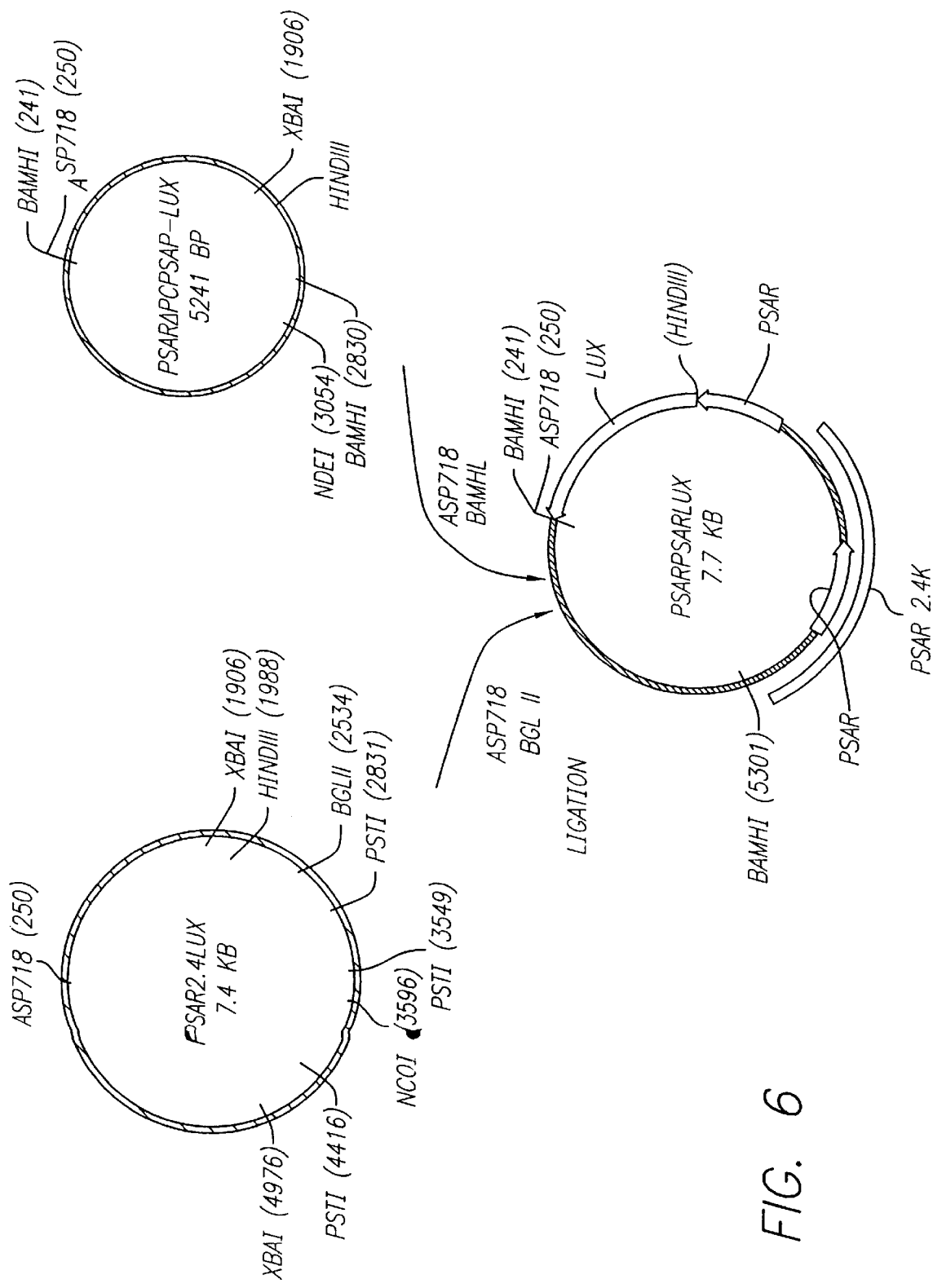
FIG. 6 is a diagram of the construction of the plasmid containing two PSAR sequences.

The PSAR-Lux fragment was recovered from our previously constructed plasmid PSARΔPCPSA-Lux (Example 1) using restriction endonuclease digestion (FIG. 6). This fragment was used to replace the DNA stretch of PCPSA promoter and luciferase gene in PSAR2.4K-PCPSA-Lux. The resulting plasmid is approximately 7.7 kb, and contains two PSAR sequences, a luciferase gene and sequences from plasmid pUCBM20 (purchased from Boehringer Mannheim, Indianapolis Ind., U.S.A.).

Tissue Specificity and Androgen Responsiveness of the Plasmid Containing Two PSAR Sequences The constructed plasmid PSAR-PSAR-Lux was used to transfect PSA-producing prostate cell line LNCaP, non-PSA-producing prostate cell lines DU145 and PC-3, and renal cell carcinoma cell line R11. Cells were maintained in RPMI 1640 medium supplemented with 10% fetal bovine serum (FBS) in T175 flasks. Cells were collected when they reached 75–85% confluency. The cells were washed in electroporation (EP) medium (1.2×RPMI, 20% FBS) twice and were resuspended in electroporation medium at $2 \times 10^7$ cells/ml. DNA of 10 μg were added to $5 \times 10^6$ cells/0.25 ml and the cells were incubated in ice for 5 minutes. The method of electroporation was as described in Example 1. After electroporation the $5 \times 10^6$ cells for each plasmid were distributed to 6 wells in 6-well cell culture plates and 2 ml RPMI medium supplemented with charcoal stripped FBS and appropriate concentrations (0, 10 nM and 100 nM) of dihydrotestosterone (DHT) were added to each well.

Results

Figure 7A:
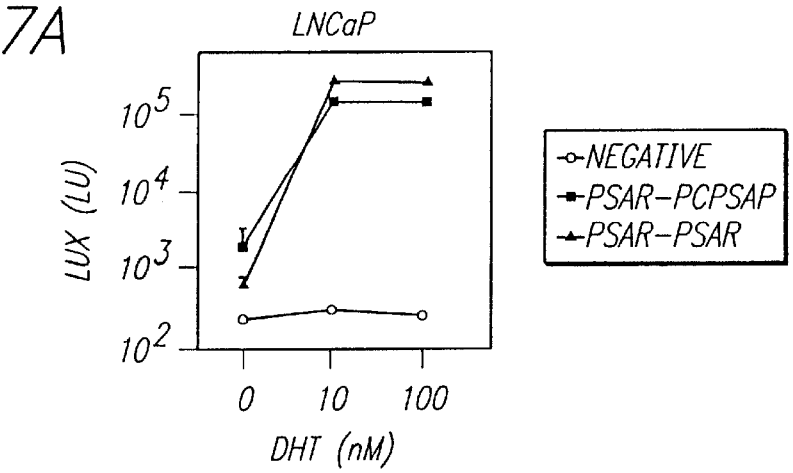
FIG. 7A is a ling graph demonstrating lux gene expression in response to DHT stimulation in LNCaP cells transfected by electroporation with plasmids having no promoter, having PSAR-PCPSA promoter or having two PSAR sequences.
Figure 7B:
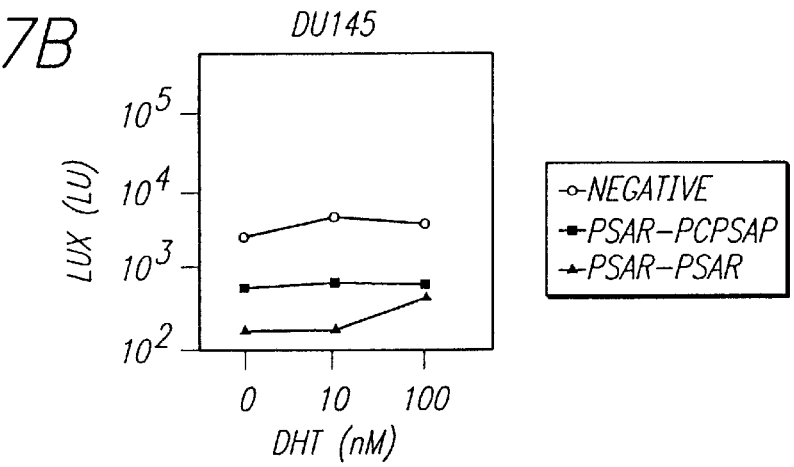
FIG. 7B is a line graph demonstrating lux gene expression in response to DHT stimulation in DU145 cells transfected by electroporation with plasmids having no promoter, having PSAR-PCPSA promoter or having two PSAR sequences.
Figure 7C:
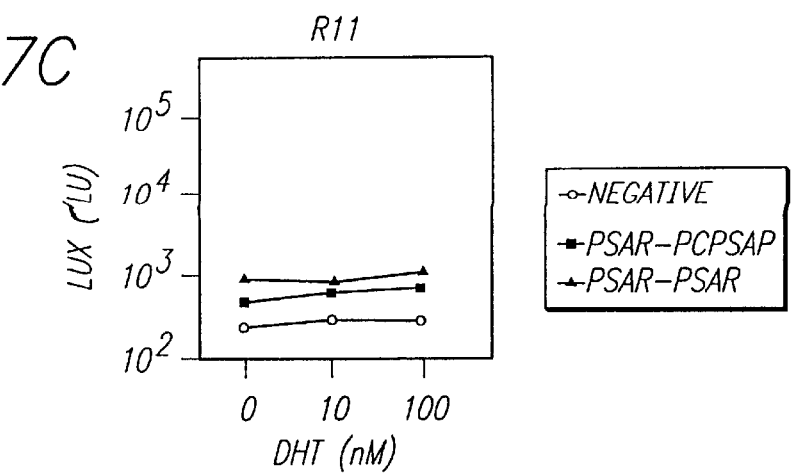
FIG. 7C is a line graph demonstrating lux gene expression in response to DHT stimulation in R11 cells transfected by electroporation with plasmids having no promoter, having PSAR-PCPSA promoter or having two PSAR sequences.

As FIGS. 7A–C demonstrate, with the addition of 10 nM DHT, both PSAR-PCPSAP-Lux and PSAR 2.4 k-PSAR-Lux showed 120- to more than 1000-fold higher activity in the PSA-producing cell line LNCaP compared with non-PSA producing prostate cell lines DU145 and PC3, or R11 renal carcinoma cell line. The baseline of LNCaP (0 nM DHT) was slightly increased compared with the results shown in Example 1. In our previous experiments, LNCaP and other cells were maintained in RPMI medium with charcoal stripped medium for 3 to 7 days to turn off the expression of androgen receptor. The modification of experimental conditions may cause such slightly higher background.

We also tested a liposome-mediated DNA transfection method. Cells of $3 \times 10^5$ were plated to each well of 6-well cell culture plates 24 hours prior to DNA transfection and washed with serum-free RPMI medium before transfection. Five μg DNA were added to 0.5 ml serum-free RPMI medium and subsequently mixed with 0.5 ml RPMI medium containing 10 μl DMRIE/DOPE (0.747 mM, provided by Vical, San Diego, Calif.). The DNA-liposome mixture was added to each well of cells and incubated for 4 hours before 0.5 ml RPMI medium with 30% FBS were added. At 48 hours post-transfection, the cells were collected for luciferase assay.

Figure 8:
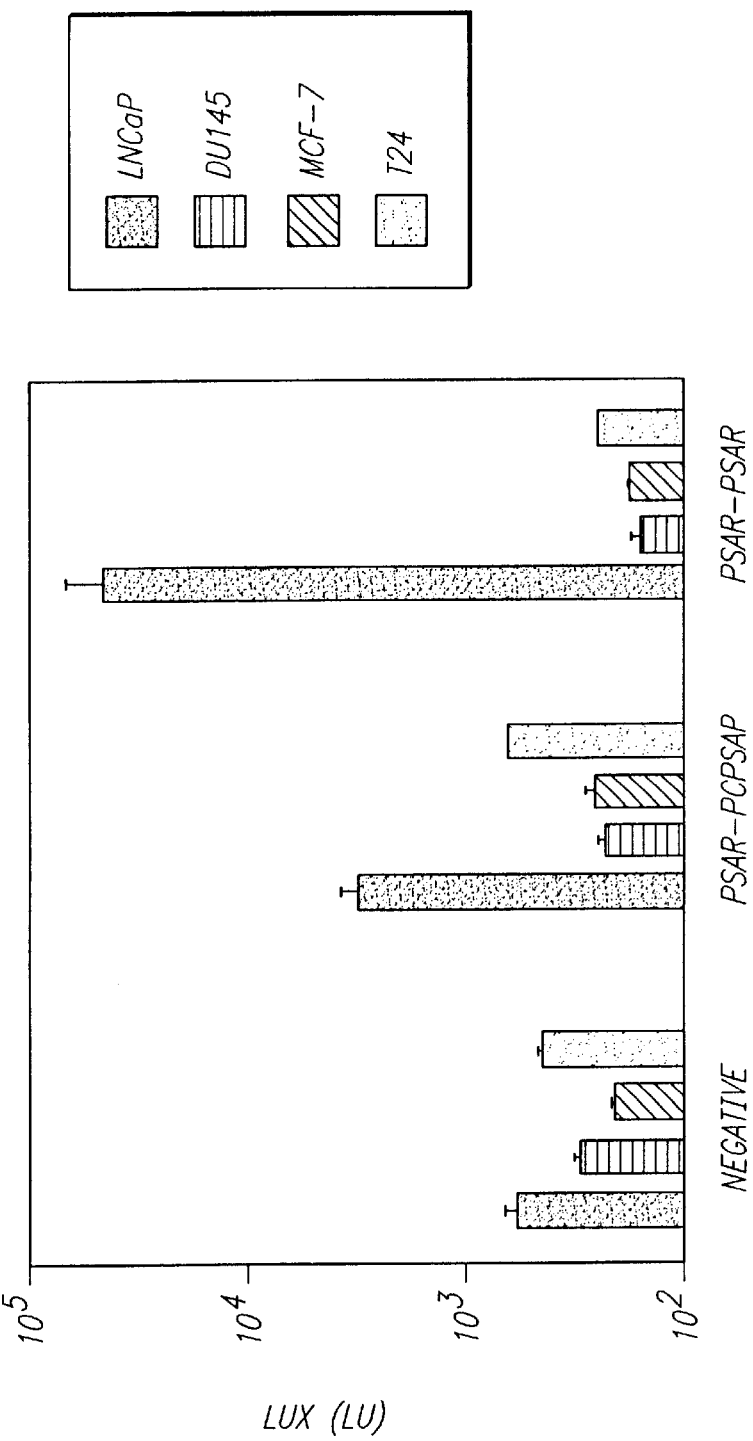
FIG. 8 is a bar graph depicting lux gene expression in LNCaP cells, DU145 cells, MCF-7 cells and T24 cells transfected by liposome-mediated transfection with plasmids having no promoter, having PSAR-PCPSA promoter or having two PSAR sequences.

As FIG. 8 shows, plasmid PSAR2.4 k-PSAR-Lux demonstrates significantly higher expression in LNCaP prostate cells as compared to non-PSA-producing cells.

Our results demonstrate that a plasmid with two PSAR fragments in tandem orientation show similar or even higher activity compared with the plasmid containing PSAR-PCPSAP expression promoter. Therefore, with the addition of PSAR, promoter activity, tissue specificity and androgen responsiveness can be significantly enhanced. We are working on plasmids containing 3 or 4 PSAR fragments and we expect that these new constructs will demonstrate even higher expression and tissue specificity. This discovery will be very useful to develop a more specific gene delivery vector for prostate cancer gene therapy.

EXAMPLE 3

This example describes the injection of a PSAR-PCPSA-Lux adenoviral vector into prostate cancer tumors in SCID mice to demonstrate the tissue specificity of PSAR in vivo.

Materials and Methods

The PSAR-PCPSA-P-Lux construct of FIG. 1 was cloned into a type 5 adenoviral vector (Microbix Biosystems, Inc., Ontario, Canada). $10^9$ plaque forming units (pfu) of the viral construct, PSAR-PCPSA-Lux-AdV, in 100 μl phosphate buffered saline (PBS) were injected into prostate cancer tumors in SCID mice (UCLA Animal Care Facility). The prostate cancer tumors were established by subcutaneous injection of approximately $10^6$–$10^7$ LAPC4 cells. The LAPC4 cell line was derived from a patient prostatic tumor. The vector was injected one and one-half months following injection of the LAPC4 cells, which is sufficient time for the tumors to reach approximately 0.5 cm in diameter. The infected mice were sacrificed 7 days post-infection. The organs and infected tumors were harvested for luciferase assay (Promega, Madison, Wis.) in accordance with the manufacturer's instructions. Tumors in control mice were infected under the same conditions with an adenovirus carrying a ctyomegalovirus (CMV) promoter driven luciferase gene. The organs and infected tumors of the control mice were harvested 3 days post-infection.

Results

Figure 9:
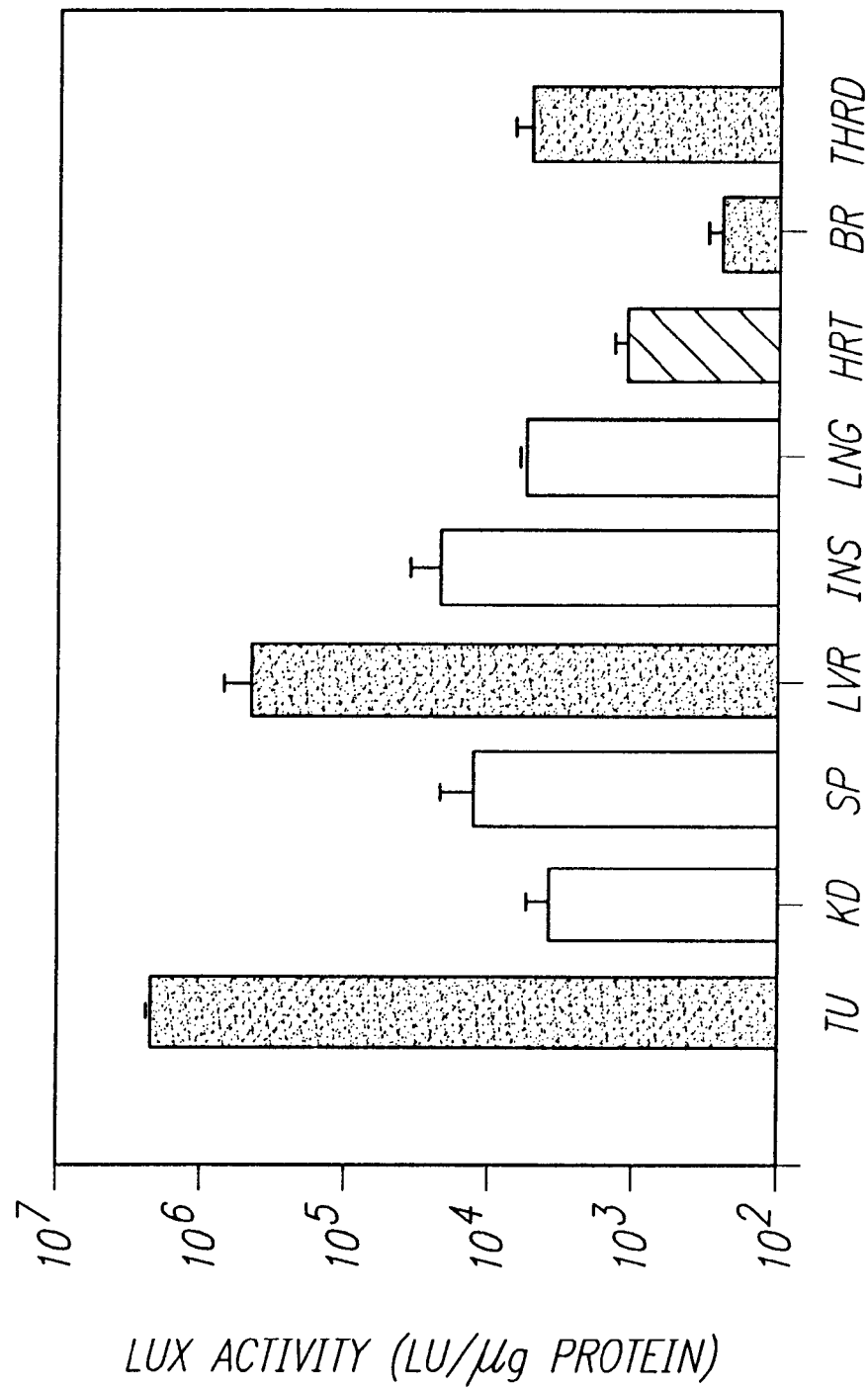
FIG. 9 is a bar graph showing luciferase activity in tumor (Tu), kidney (Kd), spleen (Sp), liver (Liv), intestine (Ins), lung (Lng), heart (Hrt), brain (Br) and thyroid (Thrd) of SCID mice injected with adenovirus carrying a CMV promoter with a luciferase gene.

The results for control animals are presented in FIG. 9 (n=3), which shows luciferase activity (in light units per μg protein) in tumor (Tu), kidney (Kd), spleen (Sp), liver (Liv), intestine (Ins), lung (Lng), heart (Hrt), brain (Br) and thyroid (Thrd). CMV promoter driven expression was high in liver as well as tumor of control animals.

Figure 10:
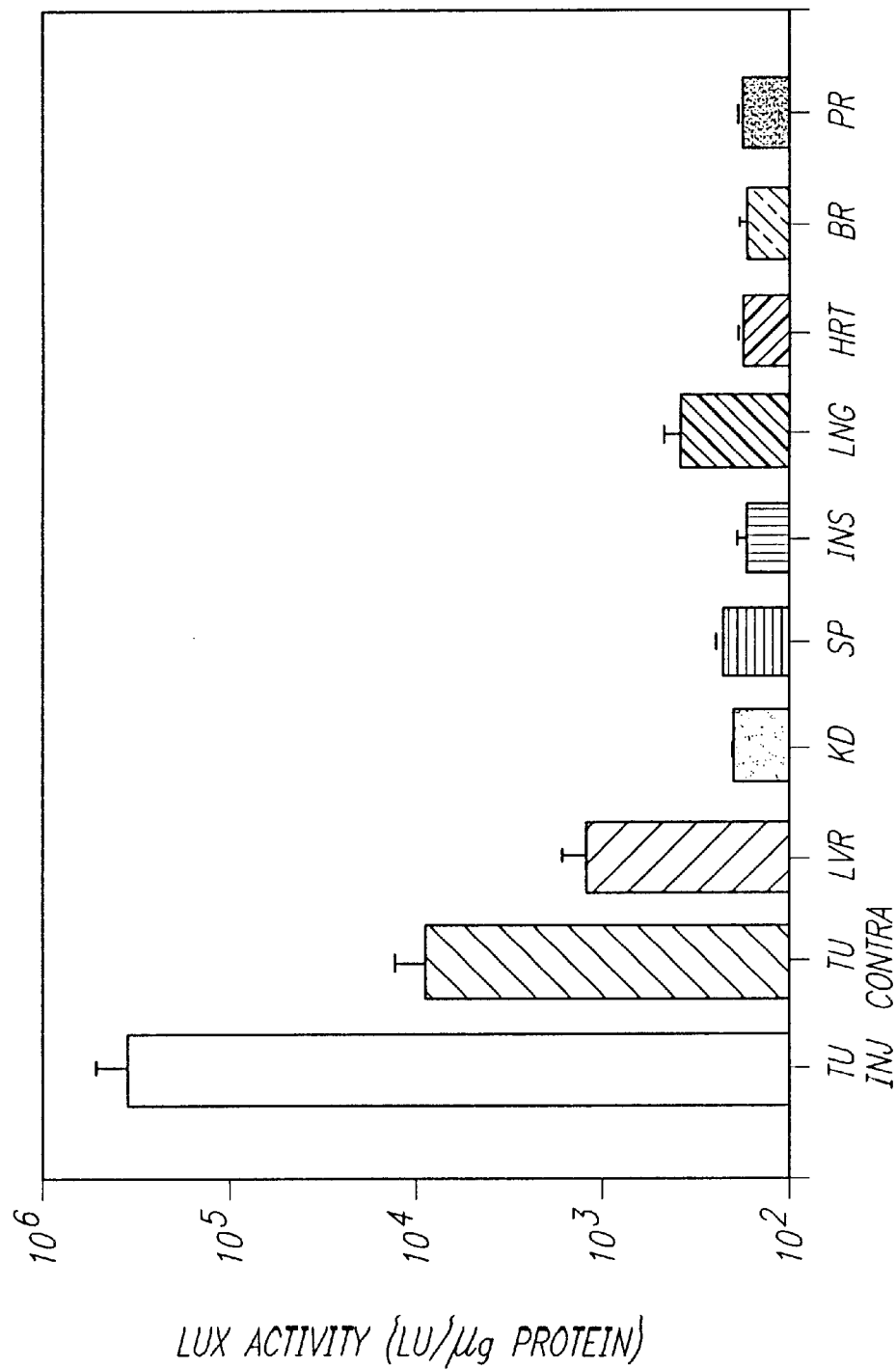
FIG. 10 is a bar graph showing luciferase activity (log scale) for the injected tumor (Tu inj), a tumor established contralateral to the injection (Tu Contra), liver (Liv), kidney (Kd), spleen (Sp), intestine (Ins), lung (Lng), heart (Hrt), brain (Br) and prostate (Pr) of mice infected with PSAR-PCPSA-Lux-AdV.

In contrast, luciferase expression was much more tissue specific in mice infected with PSAR-PCPSA-Lux-AdV. FIG. 10 (n=6) shows luciferase activity (log scale) for these animals in the injected tumor (Tu inj), a tumor established contralateral to the injection (Tu Contra), liver (Liv), kidney (Kd), spleen (Sp), intestine (Ins), lung (Lng), heart (Hrt), brain (Br) and prostate (Pr). Luciferase expression was extremely high in the injected tumor. Futhermore, the contralateral tumor showed 10-fold greater expression than liver. The low level of expression in SCID mouse prostate is not unexpected because mice lack a gene comparable to PSA.

These results confirm the tissue specificity of PSAR-PCPSA-P driven transgene expression in vivo. This strongly suggests that a tissue-specific promoter provides a safe and specific approach for prostate cancer gene therapy.

What is claimed is:

1. An isolated nucleic acid molecule which is designated PSAR, consisting of SEQ ID NO: 3.

2. The nucleic acid molecule of claim 1 having ATCC Accession No. 97495.

3. A vector comprising the nucleic acid molecule of claim 1 and a gene of interest, wherein the gene is positioned downstream of the PSAR.

4. The vector of claim 3 further comprising an additional PSA promoter that is positioned upstream of the gene of interest.

5. The vector of claim 3 further comprising a second PSAR consisting of SEQ ID NO: 3.

6. The vector of claim 3, wherein the vector is a viral vector.

7. The vector of claim 6, wherein the viral vector is a retrovirus vector, an adenovirus vector, an adeno-associated virus vector, a vaccinia virus vector, a herpes virus vector or a rabies virus vector.

8. The vector of claim 3, wherein the vector is a non-viral vector.

9. The vector of claim 8, wherein the vector is a plasmid.

10. The vector of claim 3, wherein the gene of interest is a suicide gene.

11. The vector of claim 10, wherein the suicide gene is a thymidine kinase gene.

12. The vector of claim 3, wherein the gene of interest is a tumor suppressor gene.

13. The vector of claim 3, wherein the gene of interest encodes a growth factor.

14. The vector of claim 3, wherein the gene of interest encodes a cytokine.

15. The vector of claim 14, wherein the cytokine is an interferon.

16. The vector of claim 14, wherein the cytokine is a colony stimulating factor.

17. The vector of claim 16, wherein the colony stimulating factor is a granulocyte colony stimulating factor.

18. The vector of claim 16, wherein the colony stimulating factor is a granulocyte macrophage colony stimulating factor.

19. The vector of claim 3, wherein the gene of interest encodes a toxin.

20. The vector of claim 3, wherein the gene of interest encodes an antibody.

21. A host vector system comprising the vector of claim 3 in a host cell.

22. The host vector system of claim 21, wherein the host cell is a bacterial cell.

23. The host vector system of claim 21, wherein the host cell is a eucaryotic cell.

24. The host vector system of claim 23, wherein the eucaryotic cell is a PSA-producing cell.

25. The host vector system of claim 23, wherein the eucaryotic cell is an animal cell.

26. The host vector system of claim 25, wherein the animal cell is a human cell.

27. A method for producing a protein comprising culturing the host vector system of claim 21 so as to produce the protein encoded by the gene in the host.

28. A method for producing a protein comprising:
   (a) introducing a vector into a PSA-producing cell, the vector comprising the nucleic acid sequence of claim 1 and a gene encoding the protein; and
   (b) culturing the PSA-producing cell into which the vector has been introduced under sufficient conditions so that the protein is produced.

29. The method of claim 28, wherein the vector further comprises another nucleic acid sequence consisting of the sequence of SEQ ID NO: 3.

30. The method of claim 27, 28 or 29, wherein the gene is a suicide gene.

31. The method of claim 30, wherein the suicide gene is a thymidine kinase gene.

32. The method of claim 27, 28 or 29, wherein the protein is a tumor suppressor.

33. The method of claim 27, 28 or 29, wherein the protein is a growth factor.

34. The method of claim 27, 28 or 29, wherein the protein is a cytokine.

35. The method of claim 34, wherein the cytokine is an interferon.

36. The method of claim 34, wherein the cytokine is a colony stimulating factor.

37. The method of claim 36, wherein the colony stimulating factor is a granulocyte colony stimulating factor.

38. The method of claim 36, wherein the colony stimulating factor is a granulocyte macrophage colony stimulating factor.

39. The method of claim 27, 28 or 29, wherein the protein is a toxin.

40. The method of claim 27, 28 or 29, wherein the protein is an antibody.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 28 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

CTTTTAGTAT GCGGCCGCTC TAGAAATC                                       28

(2) INFORMATION FOR SEQ ID NO:2:

(i) SEQUENCE CHARACTERISTICS:
       (A) LENGTH: 32 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:2:

CCTGGGTAGT CCTTTTACAA GATCTGGTGG AG                              32

(2) INFORMATION FOR SEQ ID NO:3:

(i) SEQUENCE CHARACTERISTICS:
       (A) LENGTH: 822 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:3:

CTGCAGAGAA ATTAATTGTG GCCTGATGTC CCTGTCCTGG AGAGGGTGGA GGTGGACCTT    60

CACTAACCTC CTACCTTGAC CCTCTCTTTT AGGGCTCTTT CTGACCTCCA CCATGATACT   120

AGGACCCCAT TGTATTCTGT ACACTCTTGA CTCTATGACC CCCACTGCCC ACTGCATCCA   180

GCTGGGTCCC CTCCTATCTC TATTCCCAGC TGGCCAGTGC AGTCTCAGTG CCCACCTGTT   240

TGTCAGTTAC TCTGAAGGGG CTGACATTTT ACTGACTTGC AAACAAATAA GCTAACTTTC   300

CAGAGTTTTG TGAATGTTGG CAGAGTCCAT GAGACTCCTG AGTCAGAGGC AAAGGCTTTT   360

ACTGCTCACA GCTTAGCAGA CAGCATGAGG TTCATGTTCA CATTAGTACA CCTTGCCCCC   420

```
CCCAAATCTT GTAGGGTGAC CAGAGCAGTC TAGGTGGATG CTGTGCACAC GGGGTTTGTG      480

CCACTGGTGA GAAACCTGAG ATTAGGAATC CTCAATCTTA TACTGGGACA ACTTGCAAAC      540

CTGCTCAGCC TTTGTCTCTG ATGAAGATAT TATCTTCATG ATCTTGGATT GAAAACAGAC      600

CTACTCTGGA GGAACATATT GTATTGATTG TCCTTGACAG TAAACAAATC TGTTGTAAGA      660

GACATTATCT TTATTATCTA GGACAGTAAG CAAGCCTGGA TCTGAGAGAG ATATCATCTT      720

GCAAGGATGC CTGCTTTACA AACATCCTTG AAACAACAAT CCAGAAAAAA AGGTGTTGCT      780

GTCTTTGCTC AGAAGACACA CAGATACGTG ACAGAACCAT GG                        822

(2) INFORMATION FOR SEQ ID NO:4:

(i) SEQUENCE CHARACTERISTICS:
        (A) LENGTH: 824 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

CTGCAGAGAA ATTAATTGTG GCCTGATGTC CCTGTCCTGG AGAGGGTGGA GGTGGACCTT       60

CACTAACCTC CTACCTTGAC CCTCTCTTTT AGGGCTCTTT CTGACCTCCA CCATGGTACT      120

AGGACCCCAT TGTATTCTGT ACCCTCTTGA CTCTATGACC CCCACTGCCC ACTGCATCCA      180

GCTGGGTCCC CTCCTATCTC TATTCCCAGC TGGCCAGTGC AGTCTCAGTG CCCACCTGTT      240

TGTCAGTAAC TCTGAAGGGG CTGACATTTT ACTGACTTGC AAACAAATAA GCTAACTTTC      300

CAGAGTTTTG TGAATGCTGG CAGAGTCCAT GAGACTCCTG AGTCAGAGGC AAAGGCTTTT      360

ACTGCTCACA GCTTAGCAGA CAGCATGAGG TTCATGTTCA CATTAGTACA CCTTGCCCCC      420

CCCAAATCTT GTAGGGTGAC CAGAGCAGTC TAGGTGGATG CTGTGCAGAA GGGGTTTGTG      480

CCACTGGTGA GAAACCTGAG ATTAGGAATC CTCAATCTTA TACTGGGACA ACTTGCAAAC      540

CTGCTCAGCC TTTGTCTCTG ATGAAGATAT TATCTTCATG ATCTTGGATT GAAAACAGAC      600

CTACTCTGGA GGAACATATT GTATCGATTG TCCTTGACAG TAAACAAATC TGTTGTAAGA      660

GACATTATCT TTATTATCTA GGACAGTAAG CAAGCCTGGA TCTGAGAGAG ATATCATCTT      720

GCAAGGATGC CTGCTTTACA AACATCCTTG AAACAACAAT CCAGAAAAAA AAGGTGTTG      780

CTGTCTTTGC TCAGAAGACA CACAGATACG TGACAGAACC ATGG                      824
```